United States Patent
Luo et al.

(10) Patent No.: US 8,053,421 B2
(45) Date of Patent: *Nov. 8, 2011

(54) DNA VACCINES AGAINST TUMOR GROWTH AND METHODS OF USE THEREOF

(75) Inventors: Yunping Luo, San Diego, CA (US); Rong Xiang, San Diego, CA (US); Ralph A. Reisfeld, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 114 days.

This patent is subject to a terminal disclaimer.

(21) Appl. No.: 12/462,496

(22) Filed: Aug. 4, 2009

(65) Prior Publication Data

US 2010/0136058 A1    Jun. 3, 2010

Related U.S. Application Data

(63) Continuation of application No. 10/574,752, filed as application No. PCT/US2004/033137 on Oct. 7, 2004, now Pat. No. 7,569,552.

(60) Provisional application No. 60/509,457, filed on Oct. 8, 2003.

(51) Int. Cl.
*A61K 48/00* (2006.01)
*C12N 15/74* (2006.01)

(52) U.S. Cl. .... 514/44; 424/93.2; 424/93.21; 435/320.1

(58) Field of Classification Search .................. None
See application file for complete search history.

(56) References Cited

U.S. PATENT DOCUMENTS

| | | | |
|---|---|---|---|
| 7,132,407 B2 * | 11/2006 | Lai et al. ............. | 514/44 R |
| 7,569,552 B2 * | 8/2009 | Luo et al. ............ | 514/44 R |

OTHER PUBLICATIONS

Weth et al. Cancer Gene Ther 2001;8:599-611.*
Zajchowski et al. Cancer Res 2001;61:5168-78.*
Asad et al. Mole Ther 2002;5:609-16.*
Luo et al. PNAS 2003;100:8850-5.*
Rosenkranz et al. Vaccine Jan. 2003;21:798-801.*
Darnell et al. Nat Rev Cancer 2002;2:740-9.*

* cited by examiner

*Primary Examiner* — Q. Janice Li
(74) *Attorney, Agent, or Firm* — Olson & Cepuritis, Ltd.

(57) ABSTRACT

A DNA vaccine suitable for eliciting an immune response against cancer cells comprises a polynucleotide construct operably encoding an a Fra-1 protein, such as a polyubiquitinated human Fra-1 protein, and IL-18, such as human IL-18, in a pharmaceutically acceptable carrier. In a preferred embodiment, the polynucleotide construct is operably incorporated in an attenuated bacterial vector, such as an attenuated *Salmonella typhimurium*, particularly a doubly attenuated aroA$^-$ dam$^-$ *S. typhimurium*. Transformed host cells, methods of inhibiting tumor growth, of vaccinating a patient against cancer, and of delivering genetic material to a mammalian cell in vivo are also described.

21 Claims, 14 Drawing Sheets

A

Suppression of lung metastases of D2F2 by oral DNA vaccine

| Treatment groups | Metastasis Score |
|---|---|
| A. Empty vector | 2 3 3 3 3 3 3 3 |
| B. pUb | 3 3 3 3 3 3 3 3 |
| C. pUb-Fra-1 | 1 1 2 2 2 2 2 3 |
| D. pIL-18 | 0 0 1 1 1 2 2 2 |
| E. pUb-Fra-1/pIL-18 | 0 0 0 0 0 1 1 2 |

Homo sapiens - Fra-1

VERSION    NM_005438.1  GI:4885242

```
  1 agccgtgtac cccgcagagc cgccagcccc gggcatgttc cgagacttcg gggaacccgg
 61 cccgagctcc gggaacggcg gcgggtacgg cggccccgcg cagcccccgg ccgcagcgca
121 ggcagcccag cagaagttcc acctggtgcc aagcatcaac accatgagtg gcagtcagga
181 gctgcagtgg atggtacagc ctcatttcct ggggcccagc agttacccca ggcctctgac
241 ctaccctcag tacagccccc cacaaccccg gccaggagtc atccgggccc tggggccgcc
301 tccaggggta cgtcgaaggc cttgtgaaca gatcagcccg gaggaagagg agcgccgccg
361 agtaaggcgc gagcggaaca agctggctgc ggccaagtgc aggaaccgga ggaaggaact
421 gaccgacttc ctgcaggcgg agactgacaa actggaagat gagaaatctg ggctgcagcg
481 agagattgag gagctgcaga agcagaagga gcgcctagag ctggtgctgg aagcccaccg
541 acccatctgc aaaatcccgg aaggagccaa ggagggggac acaggcagta ccagtggcac
601 cagcagccca ccagcccct gccgccctgt accttgtatc tcccttttccc cagggcctgt
661 gcttgaacct gaggcactgc acaccccac actcatgacc acaccctccc taactccttt
721 cacccccagc ctggtcttca cctacccag cactcctgag ccttgtgcct cagctcatcg
781 caagagtagc agcagcagcg gagacccatc ctctgacccc cttggctctc caaccctcct
841 cgctttgtga ggcgcctgag ccctactccc tgcagatgcc accctagcca atgtctcctc
901 cccttccccc accggtccag ctggcctgga cagtatccca catccaactc cagc
    (SEQ ID NO: 1)
```

Homo sapiens - Fra-1

MFRDFGEPGPSSGNGGGYGGPAQPPAAAQAAQQKFHLVPSINTMSGSQELQWMVQPHFLGPSSYPRPLTY
PQYSPPQPRPGVIRALGPPPGVRRRPCEQISPEEEERRRVRRERNKLAAAKCRNRRKELTDFLQAETDKL
EDEKSGLQREIEELQKQKERLELVLEAHRPICKIPEGAKEGDTGSTSGTSSPPAPCRPVPCISLSPGPVL
EPEALHTPTLMTTPSLTPFTPSLVFTYPSTPEPCASAHRKSSSSSGDPSSDPLGSPTLLAL
(SEQ ID NO: 2)

FIG. 10

Murine Fra-1

(DNA Sequence, SEQ ID NO: 3; Protein Sequence, SEQ ID NO: 4)

```
  1 ATGTACCGAGACTACGGGGAACCGGGACCGAGCTCCGGGGCTGGCAGCGCGTACGGTCGC   60
  1  M  Y  R  D  Y  G  E  P  G  P  S  S  G  A  G  S  A  Y  G  R   20

61 CCCGCGCAGCCCCCGCAAGCTCAGGCACAGACCGCCCAGCAGCAGAAGTTCCACTTTGTG  120
 21  P  A  Q  P  P  Q  A  Q  A  Q  T  A  Q  Q  Q  K  F  H  F  V   40

121 CCAAGCATCGACAGCAGCAGCCAGGAACTGCACTGGATGGTGCAGCCTCATTTCCTGGGA  180
 41  P  S  I  D  S  S  S  Q  E  L  H  W  M  V  Q  P  H  F  L  G   60

181 CCCACTGGCTATCCCCGACCTCTGGCCTATCCCCAGTACAGTCCCCCTCAGCCCCGGCCA  240
 61  P  T  G  Y  P  R  P  L  A  Y  P  Q  Y  S  P  P  Q  P  R  P   80

241 GGAGTCATACGAGCCCTAGGGCCACCTCCGGGGGTGCGTCGCAGGCCCTGCGAGCAGATC  300
 81  G  V  I  R  A  L  G  P  P  P  G  V  R  R  R  P  C  E  Q  I  100

301 AGCCCAGAGGAGGAAGAGCGCCGCAGGGTGAGACGCGAGCGGAACAAGCTAGCAGCTGCT  360
101  S  P  E  E  E  E  R  R  R  V  R  R  E  R  N  K  L  A  A  A  120

361 AAGTGCAGAAACCGAAGAAAGGAGCTGACAGACTTCCTGCAGGCGGAGACCGACAAATTG  420
121  K  C  R  N  R  R  K  E  L  T  D  F  L  Q  A  E  T  D  K  L  140

421 GAGGATGAGAAATCGGGGCTGCAGCGAGAGATTGAAGAGCTGCAGAAGCAGAAGGAACGC  480
141  E  D  E  K  S  G  L  Q  R  E  I  E  E  L  Q  K  Q  K  E  R  160

481 CTTGAGCTGGTGCTGGAAGCCCATCGCCTCATCTGCAAAATCCCAGAAGGAGACAAGAAG  540
161  L  E  L  V  L  E  A  H  R  L  I  C  K  I  P  E  G  D  K  K  180

541 GACCCAGGTGGTTCTGGCAGCACCAGCGGGGCTAGCAGCCCACCAGCCCCCGGCCGCCCA  600
181  D  P  G  G  S  G  S  T  S  G  A  S  S  P  P  A  P  G  R  P  200

601 GTGCCTTGCATCTCCCTTTCTCCAGGACCCGTACTTGAACCGGAAGCACTGCATACCCCC  660
201  V  P  C  I  S  L  S  P  G  P  V  L  E  P  E  A  L  H  T  P  220

661 ACGCTCATGACCACACCCTCTCTGACTCCTTTTACTCCGAGTCTGGTTTTCACCTATCCT  720
221  T  L  M  T  T  P  S  L  T  P  F  T  P  S  L  V  F  T  Y  P  240

721 AGCACACCAGAACCTTGCTCCTCCACTCACCGAAAGAGTAGCAGCAGCAGTGGCGACCCC  780
241  S  T  P  E  P  C  S  S  T  H  R  K  S  S  S  S  G  D  P  260

781 TCCTCCGACCCCCTGGGCTCTCCTACACTCCTGGCTTTGTGA                    822
261  S  S  D  P  L  G  S  P  T  L  L  A  L  *                    274
```

FIG. 11

Homo sapiens - IL-18

VERSION     NM_001562.2  GI:27502389

```
   1 attctctccc cagcttgctg agccctttgc tcccctggcg actgcctgga cagtcagcaa
  61 ggaattgtct cccagtgcat tttgccctcc tggctgccaa ctctggctgc taaagcggct
 121 gccacctgct gcagtctaca cagcttcggg aagaggaaag gaacctcaga ccttccagat
 181 cgcttcctct cgcaacaaac tatttgtcgc aggaataaag atggctgctg aaccagtaga
 241 agacaattgc atcaactttg tggcaatgaa atttattgac aatacgcttt actttatagc
 301 tgaagatgat gaaaacctgg aatcagatta ctttggcaag cttgaatcta aattatcagt
 361 cataagaaat ttgaatgacc aagttctctt cattgaccaa ggaaatcggc ctctatttga
 421 agatatgact gattctgact gtagagataa tgcaccccgg accatattta ttataagtat
 481 gtataaagat agccagccta gaggtatggc tgtaactatc tctgtgaagt gtgagaaaat
 541 ttcaactctc tcctgtgaga acaaaattat ttcctttaag gaaatgaatc ctcctgataa
 601 catcaaggat acaaaaagtg acatcatatt ctttcagaga agtgtcccag acatgataaa
 661 taagatgcaa tttgaatctt catcatacga aggatacttt ctagcttgtg aaaaagagag
 721 agacctttt aaactcattt tgaaaaagaa ggatgaattg ggggatagat ctataatgtt
 781 cactgttcaa aacgaagact agctattaaa atttcatgcc gggcgcagtg gctcacgcct
 841 gtaatcccag ccctttggga ggctgaggcg ggcagatcac cagaggtcag gtgttcaaga
 901 ccagcctgac caacatggtg aaacctcatc tctactaaaa atacaaaaaa ttagctgagt
 961 gtagtgacgc atgccctcaa tcccagctac tcaagaggct gaggcaggag aatcacttgc
1021 actccggagg tagaggttgt ggtgagccga gattgcacca ttgcgctcta gcctgggcaa
1081 caacagcaaa actccatctc aaaaaataaa ataaataaat aaacaaataa aaaattcata
1141 atgtg    (SEQ ID NO: 5)
```

Homo sapiens - IL-18

MAAEPVEDNCINFVAMKFIDNTLYFIAEDDENLESDYFGKLESKLSVIRNLNDQVLFIDQGNRPLFEDMT
DSDCRDNAPRTIFIISMYKDSQPRGMAVTISVKCEKISTLSCENKIISFKEMNPPDNIKDTKSDIIFFQR
SVPGHDNKMQFESSSYEGYFLACEKERDLFKLILKKEDELGDRSIMFTVQNED
(SEQ ID NO: 6)

FIG. 12

Murine IL-18
(DNA Sequence, SEQ ID NO: 7; Protein Sequence, SEQ ID NO: 8)

```
  1 ATGGCTGCCATGTCAGAAGACTCTTGCGTCAACTTCAAGGAAATGATGTTTATTGACAAC    60
  1  M  A  A  M  S  E  D  S  C  V  N  F  K  E  M  M  F  I  D  N    20

61 ACGCTTTACTTTATACCTGAAGAAAATGGAGACCTGGAATCAGACAACTTTGGCCGACTT   120
 21  T  L  Y  F  I  P  E  E  N  G  D  L  E  S  D  N  F  G  R  L    40

121 CACTGTACAACCGCAGTAATACGGAATATAAATGACCAAGTTCTCTTCGTTGACAAAAGA   180
 41  H  C  T  T  A  V  I  R  N  I  N  D  Q  V  L  F  V  D  K  R    60

181 CAGCCTGTGTTCGAGGATATGACTGATATTGATCAAAGTGCCAGTGAACCCCAGACCAGA   240
 61  Q  P  V  F  E  D  M  T  D  I  D  Q  S  A  S  E  P  Q  T  R    80

241 CTGATAATATACATGTACAAAGACAGTGAAGTAAGAGGACTGGCTGTGACCCTCTCTGTG   300
 81  L  I  I  Y  M  Y  K  D  S  E  V  R  G  L  A  V  T  L  S  V   100

301 AAGGATAGTAAAATGTCTACCCTCTCCTGTAAGAACAAGATCATTTCCTTTGAGGAAATG   360
101  K  D  S  K  M  S  T  L  S  C  K  N  K  I  I  S  F  E  E  M   120

361 GATCCACCTGAAAATATTGATGATATACAAAGTGATCTCATATTCTTTCAGAAACGTGTT   420
121  D  P  P  E  N  I  D  D  I  Q  S  D  L  I  F  F  Q  K  R  V   140

421 CCAGGACACAACAAGATGGAGTTTGAATCTTCACTGTATGAAGGACACTTTCTTGCTTGC   480
141  P  G  H  N  K  M  E  F  E  S  S  L  Y  E  G  H  F  L  A  C   160

481 CAAAAGGAAGATGATGCTTTCAAACTCATTCTGAAAAAAAAGGATGAAAATGGGGATAAA   540
161  Q  K  E  D  D  A  F  K  L  I  L  K  K  K  D  E  N  G  D  K   180

541 TCTGTAATGTTCACTCTCACTAACTTACATCAAAGTTAG                        579
181  S  V  M  F  T  L  T  N  L  H  Q  S  *                        193
```

FIG. 13

Ubiquitin (DNA Sequence, SEQ ID NO: 9; Protein Sequence, SEQ ID NO: 10)

```
  1 ATGCAGATCTTCGTGAAGACCCTGACCGGCAAGACCATCACCCTAGAGGTGGAGCCCAGT      60
  1  M  Q  I  F  V  K  T  L  T  G  K  T  I  T  L  E  V  E  P  S      20

61 GACACCATCGAGAACGTGAAGGCCAAGATCCAGGATAAAGAGGGCATCCCCCCTGACCAG     120
 21  D  T  I  E  N  V  K  A  K  I  Q  D  K  E  G  I  P  P  D  Q      40

121 CAGAGGCTGATCTTTGCCGGCAAGCAGCTGGAAGATGGCCGCACCCTCTCTGATTACAAC     180
 41  Q  R  L  I  F  A  G  K  Q  L  E  D  G  R  T  L  S  D  Y  N      60

181 ATCCAGAAGGAGTCAACCCTGCACCTGGTCCTTCGCCTGAGAGGTGGC                 228
 61  I  Q  K  E  S  T  L  H  L  V  L  R  L  R  G  G                  76
```

FIG. 14

SEQUENCE LISTING

<160> NUMBER OF SEQ ID NOS: 10

<210> SEQ ID NO 1
<211> LENGTH: 954
<212> TYPE: DNA
<213> ORGANISM: HOMO SAPIENS

<400> SEQUENCE: 1

```
agccgtgtac cccgcagagc cgccagcccc gggcatgttc cgagacttcg gggaacccgg      60
cccgagctcc gggaacggcg gcgggtacgg cggccccgcg cagcccccgg ccgcagcgca     120
ggcagcccag cagaagttcc acctggtgcc aagcatcaac accatgagtg gcagtcagga     180
gctgcagtgg atggtacagc ctcatttcct ggggcccagc agttacccca ggcctctgac     240
ctaccctcag tacagccccc cacaacccg gccaggagtc atccgggccc tggggccgcc     300 tccagggta cgtcgaaggc cttgtgaaca gatcagcccg gaggaagagg agcgccgccg     360
agtaaggcgc gagcggaaca agctggctgc ggccaagtgc aggaaccgga ggaaggaact     420
```

```
gaccgacttc ctgcaggcgg agactgacaa actggaagat gagaaatctg ggctgcagcg    480
agagattgag gagctgcaga agcagaagga gcgcctagag ctggtgctgg aagcccaccg    540
acccatctgc aaaatcccgg aaggagccaa ggaggggggac acaggcagta ccagtggcac    600
cagcagccca ccagccccct gccgccctgt accttgtatc tcccttccc cagggcctgt     660 gcttgaacct gaggcactgc acaccccac actcatgacc acaccctccc taactccttt     720
cacccccagc ctggtcttca cctaccccag cactcctgag ccttgtgcct cagctcatcg    780
caagagtagc agcagcagcg gagacccatc ctctgacccc cttggctctc caaccctcct    840
cgctttgtga ggcgcctgag ccctactccc tgcagatgcc accctagcca atgtctcctc    900 cccttcccc accggtccag ctggcctgga cagtatccca catccaactc cagc          954
```

```
<210> SEQ ID NO 2
<211> LENGTH: 271
<212> TYPE: PRT
<213> ORGANISM: HOMO SAPIENS

<400> SEQUENCE: 2

Met Phe Arg Asp Phe Gly Glu Pro Gly Pro Ser Ser Gly Asn Gly Gly
 1               5                   10                  15

Gly Tyr Gly Gly Pro Ala Gln Pro Pro Ala Ala Ala Gln Ala Ala Gln
                20                  25                  30

Gln Lys Phe His Leu Val Pro Ser Ile Asn Thr Met Ser Gly Ser Gln
            35                  40                  45

Glu Leu Gln Trp Met Val Gln Pro His Phe Leu Gly Pro Ser Ser Tyr
        50                  55                  60

Pro Arg Pro Leu Thr Tyr Pro Gln Tyr Ser Pro Pro Gln Pro Arg Pro
65                  70                  75                  80

Gly Val Ile Arg Ala Leu Gly Pro Pro Gly Val Arg Arg Arg Pro
                85                  90                  95

Cys Glu Gln Ile Ser Pro Glu Glu Glu Arg Arg Arg Val Arg Arg
                100                 105                 110

Glu Arg Asn Lys Leu Ala Ala Ala Lys Cys Arg Asn Arg Arg Lys Glu
            115                 120                 125

Leu Thr Asp Phe Leu Gln Ala Glu Thr Asp Lys Leu Glu Asp Glu Lys
        130                 135                 140

Ser Gly Leu Gln Arg Glu Ile Glu Glu Leu Gln Lys Gln Lys Glu Arg
145                 150                 155                 160

Leu Glu Leu Val Leu Glu Ala His Arg Pro Ile Cys Lys Ile Pro Glu
                165                 170                 175

Gly Ala Lys Glu Gly Asp Thr Gly Ser Thr Ser Gly Thr Ser Ser Pro
                180                 185                 190

Pro Ala Pro Cys Arg Pro Val Pro Cys Ile Ser Leu Ser Pro Gly Pro
            195                 200                 205

Val Leu Glu Pro Glu Ala Leu His Thr Pro Thr Leu Met Thr Thr Pro
        210                 215                 220

Ser Leu Thr Pro Phe Thr Pro Ser Leu Val Phe Thr Tyr Pro Ser Thr
225                 230                 235                 240

Pro Glu Pro Cys Ala Ser Ala His Arg Lys Ser Ser Ser Ser Ser Gly
                245                 250                 255

Asp Pro Ser Ser Asp Pro Leu Gly Ser Pro Thr Leu Leu Ala Leu
                260                 265                 270
```

```
<210> SEQ ID NO 3
```

```
<211> LENGTH: 822
<212> TYPE: DNA
<213> ORGANISM: MUS MUSCULUS

<400> SEQUENCE: 3
atgtaccgag actacgggga accgggaccg agctccgggg ctggcagcgc gtacggtcgc      60
cccgcgcagc ccccgcaagc tcaggcacag accgcccagc agcagaagtt ccactttgtg     120
ccaagcatcg acagcagcag ccaggaactg cactggatgg tgcagcctca tttcctggga     180
cccactggct atccccgacc tctggcctat ccccagtaca gtcccccctca gccccggcca     240 ggagtcatac gagccctagg ccacctccg ggggtgcgtc gcaggccctg cgagcagatc      300
agcccagagg aggaagagcg ccgcagggtg agacgcgagc ggaacaagct agcagctgct     360
aagtgcagaa accgaagaaa ggagctgaca gacttcctgc aggcggagac cgacaaattg     420
gaggatgaga atcggggct gcagcgagag attgaagagc tgcagaagca aaggaacgc      480 cttgagctgg tgctggaagc ccatcgcctc atctgcaaaa tcccagaagg agacaagaag     540
gacccaggtg gttctggcag caccagcggg gctagcagcc accagccccc cggccgccca     600
gtgccttgca tctcccttc tccaggaccc gtacttgaac cggaagcact gcataccccc      660
acgctcatga ccacaccctc tctgactcct tttactccga gtctggtttt cacctatcct     720
agcacaccag aaccttgctc ctccactcac cgaaagagta gcagcagcag tggcgacccc     780
tcctccgacc ccctgggctc tcctacactc ctggctttgt ga                         822

<210> SEQ ID NO 4
<211> LENGTH: 273
<212> TYPE: PRT
<213> ORGANISM: MUS MUSCULUS

<400> SEQUENCE: 4

Met Tyr Arg Asp Tyr Gly Glu Pro Gly Pro Ser Ser Gly Ala Gly Ser
  1               5                  10                  15

Ala Tyr Gly Arg Pro Ala Gln Pro Pro Gln Ala Gln Ala Gln Thr Ala
             20                  25                  30

Gln Gln Gln Lys Phe His Phe Val Pro Ser Ile Asp Ser Ser Ser Gln
         35                  40                  45

Glu Leu His Trp Met Val Gln Pro His Phe Leu Gly Pro Thr Gly Tyr
     50                  55                  60

Pro Arg Pro Leu Ala Tyr Pro Gln Tyr Ser Pro Gln Pro Arg Pro
 65                  70                  75                  80

Gly Val Ile Arg Ala Leu Gly Pro Pro Gly Val Arg Arg Pro
                 85                  90                  95

Cys Glu Gln Ile Ser Pro Glu Glu Glu Arg Arg Val Arg Arg
                100                 105                 110

Glu Arg Asn Lys Leu Ala Ala Ala Lys Cys Arg Asn Arg Arg Lys Glu
            115                 120                 125

Leu Thr Asp Phe Leu Gln Ala Glu Thr Asp Lys Leu Glu Asp Glu Lys
        130                 135                 140

Ser Gly Leu Gln Arg Glu Ile Glu Glu Leu Gln Lys Gln Lys Glu Arg
145                 150                 155                 160

Leu Glu Leu Val Leu Glu Ala His Arg Leu Ile Cys Lys Ile Pro Glu
                165                 170                 175

Gly Asp Lys Lys Asp Pro Gly Gly Ser Gly Ser Thr Ser Gly Ala Ser
            180                 185                 190

Ser Pro Pro Ala Pro Gly Arg Pro Val Pro Cys Ile Ser Leu Ser Pro
        195                 200                 205
```

```
Gly Pro Val Leu Glu Pro Glu Ala Leu His Thr Pro Thr Leu Met Thr
    210                 215                 220

Thr Pro Ser Leu Thr Pro Phe Thr Pro Ser Leu Val Phe Thr Tyr Pro
225                 230                 235                 240

Ser Thr Pro Glu Pro Cys Ser Ser Thr His Arg Lys Ser Ser Ser Ser
                245                 250                 255

Ser Gly Asp Pro Ser Ser Asp Pro Leu Gly Ser Pro Thr Leu Leu Ala
            260                 265                 270

Leu

<210> SEQ ID NO 5
<211> LENGTH: 1145
<212> TYPE: DNA
<213> ORGANISM: HOMO SAPIENS

<400> SEQUENCE: 5
attctctccc cagcttgctg agccctttgc tcccctggcg actgcctgga cagtcagcaa      60
ggaattgtct cccagtgcat tttgccctcc tggctgccaa ctctggctgc taaagcggct     120
gccacctgct gcagtctaca cagcttcggg aagaggaaag gaacctcaga ccttccagat     180
cgcttcctct cgcaacaaac tatttgtcgc aggaataaag atggctgctg aaccagtaga     240
agacaattgc atcaactttg tggcaatgaa atttattgac aatacgcttt acttatatagc     300 tgaagatgat gaaaacctgg aatcagatta ctttggcaag cttgaatcta aattatcagt     360
cataagaaat ttgaatgacc aagttctctt cattgaccaa ggaaatcggc ctctatttga     420
agatatgact gattctgact gtagagataa tgcaccccgg accatattta ttataagtat     480
gtataaagat agccagccta gaggtatggc tgtaactatc tctgtgaagt gtgagaaaat     540
ttcaactctc tcctgtgaga acaaaattat tcctttaag gaaatgaatc ctcctgataa     600
catcaaggat acaaaaagtg acatcatatt ctttcagaga agtgtcccag acatgataa     660 taagatgcaa tttgaatctt catcatacga aggatacttt ctagcttgtg aaaaagagag     720 agacctttt aaactcattt tgaaaaaaga ggatgaattg ggggatagat ctataatgtt     780
cactgttcaa aacgaagact agctattaaa atttcatgcc gggcgcagtg gctcacgcct     840
gtaatcccag ccctttggga ggctgaggcg ggcagatcac cagaggtcag gtgttcaaga     900
ccagcctgac caacatggtg aaacctcatc tctactaaaa atacaaaaaa ttagctgagt     960
gtagtgacgc atgccctcaa tcccagctac tcaagaggct gaggcaggag aatcacttgc    1020
actccggagg tagaggttgt ggtgagccga gattgcacca ttgcgctcta gcctgggcaa    1080
caacagcaaa actccatctc aaaaaataaa ataaataaat aaacaaataa aaaattcata    1140
atgtg                                                                 1145

<210> SEQ ID NO 6
<211> LENGTH: 193
<212> TYPE: PRT
<213> ORGANISM: HOMO SAPIENS

<400> SEQUENCE: 6

Met Ala Ala Glu Pro Val Glu Asp Asn Cys Ile Asn Phe Val Ala Met
1               5                   10                  15

Lys Phe Ile Asp Asn Thr Leu Tyr Phe Ile Ala Glu Asp Asp Glu Asn
                20                  25                  30

Leu Glu Ser Asp Tyr Phe Gly Lys Leu Glu Ser Lys Leu Ser Val Ile
            35                  40                  45
```

```
Arg Asn Leu Asn Asp Gln Val Leu Phe Ile Asp Gln Gly Asn Arg Pro
 50                  55                  60

Leu Phe Glu Asp Met Thr Asp Ser Asp Cys Arg Asp Asn Ala Pro Arg
 65                  70                  75                  80

Thr Ile Phe Ile Ile Ser Met Tyr Lys Asp Ser Gln Pro Arg Gly Met
                 85                  90                  95

Ala Val Thr Ile Ser Val Lys Cys Glu Lys Ile Ser Thr Leu Ser Cys
                100                 105                 110

Glu Asn Lys Ile Ile Ser Phe Lys Glu Met Asn Pro Pro Asp Asn Ile
            115                 120                 125

Lys Asp Thr Lys Ser Asp Ile Ile Phe Phe Gln Arg Ser Val Pro Gly
130                 135                 140

His Asp Asn Lys Met Gln Phe Glu Ser Ser Tyr Glu Gly Tyr Phe
145                 150                 155                 160

Leu Ala Cys Glu Lys Glu Arg Asp Leu Phe Lys Leu Ile Leu Lys Lys
                165                 170                 175

Glu Asp Glu Leu Gly Asp Arg Ser Ile Met Phe Thr Val Gln Asn Glu
                180                 185                 190

Asp
```

<210> SEQ ID NO 7
<211> LENGTH: 579
<212> TYPE: DNA
<213> ORGANISM: MUS MUSCULUS

<400> SEQUENCE: 7

```
atggctgcca tgtcagaaga ctcttgcgtc aacttcaagg aaatgatgtt tattgacaac    60
acgctttact ttatacctga agaaaatgga gacctggaat cagacaactt tggccgactt   120
cactgtacaa ccgcagtaat acggaatata aatgaccaag ttctcttcgt tgacaaaaga   180
cagcctgtgt tcgaggatat gactgatatt gatcaaagtg ccagtgaacc ccagaccaga   240
ctgataatat acatgtacaa agacagtgaa gtaagaggac tggctgtgac cctctctgtg   300
aaggatagta aatgtctac cctctcctgt aagaacaaga tcatttcctt tgaggaaatg   360
gatccacctg aaaatattga tgatatacaa agtgatctca tattctttca gaaacgtgtt   420
ccaggacaca acaagatgga gtttgaatct tcactgtatg aaggacactt tcttgcttgc   480
caaaaggaag atgatgcttt caaactcatt ctgaaaaaaa aggatgaaaa tggggataaa   540
tctgtaatgt tcactctcac taacttacat caaagttag                          579
```

<210> SEQ ID NO 8
<211> LENGTH: 192
<212> TYPE: PRT
<213> ORGANISM: MUS MUSCULUS

<400> SEQUENCE: 8

```
Met Ala Ala Met Ser Glu Asp Ser Cys Val Asn Phe Lys Glu Met Met
  1               5                  10                  15

Phe Ile Asp Asn Thr Leu Tyr Phe Ile Pro Glu Glu Asn Gly Asp Leu
             20                  25                  30

Glu Ser Asp Asn Phe Gly Arg Leu His Cys Thr Thr Ala Val Ile Arg
         35                  40                  45

Asn Ile Asn Asp Gln Val Leu Phe Val Asp Lys Arg Gln Pro Val Phe
 50                  55                  60

Glu Asp Met Thr Asp Ile Asp Gln Ser Ala Ser Glu Pro Gln Thr Arg
 65                  70                  75                  80
```

```
Leu Ile Ile Tyr Met Tyr Lys Asp Ser Glu Val Arg Gly Leu Ala Val
                85                  90                  95

Thr Leu Ser Val Lys Asp Ser Lys Met Ser Thr Leu Ser Cys Lys Asn
            100                 105                 110

Lys Ile Ile Ser Phe Glu Glu Met Asp Pro Pro Glu Asn Ile Asp Asp
            115                 120                 125

Ile Gln Ser Asp Leu Ile Phe Phe Gln Lys Arg Val Pro Gly His Asn
        130                 135                 140

Lys Met Glu Phe Glu Ser Ser Leu Tyr Glu Gly His Phe Leu Ala Cys
145                 150                 155                 160

Gln Lys Glu Asp Asp Ala Phe Lys Leu Ile Leu Lys Lys Lys Asp Glu
                165                 170                 175

Asn Gly Asp Lys Ser Val Met Phe Thr Leu Thr Asn Leu His Gln Ser
                180                 185                 190

<210> SEQ ID NO 9
<211> LENGTH: 228
<212> TYPE: DNA
<213> ORGANISM: MUS MUSCULUS

<400> SEQUENCE: 9
atgcagatct tcgtgaagac cctgaccggc aagaccatca ccctagaggt ggagcccagt      60
gacaccatcg agaacgtgaa ggccaagatc caggataaag agggcatccc ccctgaccag     120
cagaggctga tctttgccgg caagcagctg gaagatggcc gcaccctctc tgattacaac     180
atccagaagg agtcaaccct gcacctggtc cttcgcctga gaggtggc                  228

<210> SEQ ID NO 10
<211> LENGTH: 76
<212> TYPE: PRT
<213> ORGANISM: MUS MUSCULUS

<400> SEQUENCE: 10

Met Gln Ile Phe Val Lys Thr Leu Thr Gly Lys Thr Ile Thr Leu Glu
  1               5                  10                  15

Val Glu Pro Ser Asp Thr Ile Glu Asn Val Lys Ala Lys Ile Gln Asp
             20                  25                  30

Lys Glu Gly Ile Pro Pro Asp Gln Gln Arg Leu Ile Phe Ala Gly Lys
         35                  40                  45

Gln Leu Glu Asp Gly Arg Thr Leu Ser Asp Tyr Asn Ile Gln Lys Glu
     50                  55                  60

Ser Thr Leu His Leu Val Leu Arg Leu Arg Gly Gly
 65                  70                  75
```

DNA VACCINES AGAINST TUMOR GROWTH AND METHODS OF USE THEREOF

CROSS-REFERENCE TO RELATED APPLICATIONS

This application is a continuation of U.S. patent application Ser. No. 10/574,752 filed on Apr. 6, 2006, now U.S. Pat. No. 7,569,552, which is a U.S. National Stage of PCT/US2004/033137 filed on Oct. 7, 2004, which claims benefit of U.S. Provisional Patent Application No. 60/509,457 filed on Oct. 8, 2003.

GOVERNMENTAL RIGHTS

This invention was made with government support under Department of Defense Contract No. DAMD17-02-1-0562 and DAM17-02-1-0137, and National Institutes of Health Contract No. CA 83856. The United States government has certain rights in this invention.

FIELD OF THE INVENTION

This invention relates generally to DNA vaccines encoding suitable molecules effective for eliciting an immune response against tumor cells. More particularly this invention relates to DNA vaccines encoding a Fra-1 protein and IL-18. This invention also relates to methods of using the DNA vaccines to inhibit tumor growth and immunize patients against cancer.

BACKGROUND OF THE INVENTION

Breast cancer is one of the most common malignancies in women, and is the leading cause of death among women between the ages of 40 and 55 years in the United States. During the last two decades, this cancer has been studied intensively, and recently new preventive measures and therapies have emerged, especially immunological and genetic treatments administered as adjuvant therapy after surgery, radiation, and chemotherapy. Biotherapies have produced successful results in mice with mammary carcinoma, particularly with cellular vaccines, DNA vaccines, recombinant proteins, and adoptive immunotherapy.

The progression of breast cancer is often accompanied by changes in gene expression patterns in cells of growing carcinomas, resulting in highly tumorigenic and invasive cell types. Thus, AP-1 transcription factor (Activating Protein-1) belongs to a group of factors, which define tumor progression and regulate breast cancer cell invasion and growth, as well as resistance to anti-estrogens. In addition, Fra-1 (Fos-related antigen-1), a transcription factor belonging to the AP-1 family, is overexpressed in many human and mouse carcinoma cells, including those of thyroid, kidney, esophagus and breast. Overexpression of Fra-1 in epithelial carcinoma cells greatly influences their morphology, motility and invasiveness, and activates the transcription of a number of genes. Overexpression of this transcription factor also correlates with transformation of epithelial tumor cells to a more invasive phenotype, and a close, specific association of Fra-1 expression with highly invasive breast cancer cells has been reported. Taken together, these findings suggest that overexpressed Fra-1 can serve as a potential target for active vaccination against breast cancer.

Interleukin-18 (IL-18) is a potent immunoregulatory cytokine that was initially described as an IFN-γ inducing factor. This cytokine also enhances cytokine production of T cells and/or natural killer (NK) cells and induces their proliferation and cytolytic activity. Tumor cells engineered to produce IL-18 are less tumorigenic and systemic administration of IL-18 reportedly afforded considerable therapeutic activity in several murine tumor models. In addition, IL-18 enhances cellular immune mechanisms by upregulating major histocompatibility complex (MHC) expression and by favoring the differentiation of CD4$^+$ helper T cells towards the Th1 subtype. In turn, Th1 cells secrete IL-2 and IFN-γ, which facilitate the proliferation and/or activation of CD8$^+$ cytotoxic T lymphocytes, NK cells and macrophages, all of which can contribute to tumor regression. In addition, IL-18 is a novel inhibitor of angiogenesis, sufficiently potent to suppress tumor growth by directly inhibiting fibroblast growth factor-2 (FGF-2)-induced endothelial cell proliferation. Recombinant IL-18 has been evaluated as a biological "adjuvant" in murine tumor models, and its systemic administration induced significant antitumor effects in several tumor models.

Asada et al. have reported significant antitumor effects utilizing an autologous tumor cell vaccine engineered to secrete interleukin-12 (IL-12) and IL-18 in a viral vector (*Molec. Therapy* 2002, 5(5): 609-616).

Vaccines have been utilized to provide a long term protection against a number of disease conditions by very limited administration of a prophylactic agent that stimulates an organism's immune system to destroy disease pathogens before they can proliferate and cause a pathological effect. Various approaches to vaccines and vaccinations are described in Bernard R. Glick and Jack J. Pasternak, *Molecular Biotechnology, Principles and Applications of Recombinant DNA*, Second Edition, ASM Press pp. 253-276 (1998).

Vaccination is a means of inducing the body's own immune system to seek out and destroy an infecting agent before it causes a pathological response. Typically, vaccines are either live, but attenuated, infectious agents (virus or bacteria), or a killed form of the agent. A vaccine consisting of a live bacteria or virus must be non-pathogenic. Typically, a bacterial or viral culture is attenuated (weakened) by physical or chemical treatment. Although the agent is nonvirulent, it can still elicit an immune response in a subject treated with the vaccine.

An immune response is elicited by antigens, which can be either specific macromolecules or an infectious agent. These antigens are generally either proteins, polysaccharides, lipids, or glycolipids, which are recognized as "foreign" by lymphocytes known as B cells and T cells. Exposure of both types of lymphocytes to an antigen elicits a rapid cell division and differentiation response, resulting in the formation of clones of the exposed lymphocytes. B cells produce plasma cells, which in turn, produce proteins called antibodies (Ab), which selectively bind to the antigens present on the infectious agent, thus neutralizing or inactivating the pathogen (humoral immunity). In some cases, B cell response requires the assistance of CD4 helper T cells.

The specialized T cell clone that forms in response to the antigen exposure is a cytotoxic T lymphocyte (CTL), which is capable of binding to and eliminating pathogens and tissues that present the antigen (cell-mediated or cellular immunity). In some cases, an antigen presenting cell (APC) such as a dendritic cell, will envelop a pathogen or other foreign cell by endocytosis. The APC then processes the antigens from the cells and presents these antigens in the form of a histocompatibility molecule:peptide complex to the T cell receptor (TCR) on CTLs, thus stimulating an immune response.

Humoral immunity characterized by the formation of specific antibodies is generally most effective against acute bacterial infections and repeat infections from viruses, whereas cell-mediated immunity is most effective against viral infection, chronic intracellular bacterial infection, and fungal infection. Cellular immunity is also known to protect against cancers and is responsible for rejection of organ transplants.

Antibodies to antigens from prior infections remain detectable in the blood for very long periods of time, thus affording a means of determining prior exposure to a pathogen. Upon re-exposure to the same pathogen, the immune system effectively prevents reinfection by eliminating the pathogenic agent before it can proliferate and produce a pathogenic response.

The same immune response that would be elicited by a pathogen can also sometimes be produced by a non-pathogenic agent that presents the same antigen as the pathogen. In this manner, the subject can be protected against subsequent exposure to the pathogen without having previously fought off an infection.

Not all infectious agents can be readily cultured and inactivated, as is required for vaccine formation, however. Modern recombinant DNA techniques have allowed the engineering of new vaccines to seek to overcome this limitation. Infectious agents can be created that lack the pathogenic genes, thus allowing a live, nonvirulent form of the organism to be used as a vaccine. It is also possible to engineer a relatively nonpathogenic organism such as *E. coli* to present the cell surface antigens of a pathogenic carrier. The immune system of a subject vaccinated with such a transformed carrier is "tricked" into forming antibodies to the pathogen. The antigenic proteins of a pathogenic agent can be engineered and expressed in a nonpathogenic species and the antigenic proteins can be isolated and purified to produce a "subunit vaccine." Subunit vaccines have the advantage of being stable, safe, and chemically well defined; however, their production can be cost prohibitive.

A new approach to vaccines has emerged in recent years, broadly termed genetic immunization. In this approach, a gene encoding an antigen of a pathogenic agent is operably inserted into cells in the subject to be immunized. The treated cells are transformed and produce the antigenic proteins of the pathogen. These in vivo-produced antigens then trigger the desired immune response in the host. The genetic material utilized in such genetic vaccines can be either a DNA or RNA construct. Often the polynucleotide encoding the antigen is introduced in combination with other promoter polynucleotide sequences to enhance insertion, replication, or expression of the gene.

Polynucleotide vaccines (also referred to as DNA vaccines) encoding antigen genes can be introduced into the host cells of the subject by a variety of expression systems. These expression systems include prokaryotic, mammalian, and yeast expression systems. For example, one approach is to utilize a viral vector, such as vaccinia virus incorporating the new genetic material, to innoculate the host cells. Alternatively, the genetic material can be incorporated in a plasmid vector or can be delivered directly to the host cells as a "naked" polynucleotide, i.e. simply as purified DNA. In addition, the DNA can be stably transfected into attenuated bacteria such as *Salmonella typhimurium*. When a patient is orally vaccinated with the transformed *Salmonella*, the bacteria are transported to Peyer's patches in the gut (i.e., secondary lymphoid tissues), which then stimulate an immune response.

Polynucleotide vaccines provide an opportunity to immunize against disease states that are not caused by traditional pathogens, such as genetic diseases and cancer. Typically, in a genetic cancer vaccine, antigens to a specific type of tumor cell must be isolated and then introduced into the vaccine. An effective general vaccine against a number of cancers can thus entail development of numerous individual vaccines for each type of cancer cell to be immunized against. There is an ongoing need and desire, therefore, for vaccines that can stimulate a general immune response against a variety of cancer cells.

The present invention fulfills the ongoing need for vaccines that can stimulate a general immune response against cancer cells, such as breast cancer cells, by providing a DNA vaccine encoding a Fra-1 protein and IL-18 in a single host vector.

SUMMARY OF THE INVENTION

A DNA vaccine effective for eliciting an immune response against cancer cells comprises at least one polynucleotide construct operably encoding a Fra-1 protein and IL-18 in a pharmaceutically acceptable carrier. Preferably, the polynucleotide construct is operably incorporated in a host vector such as an attenuated bacterial vector (e.g, an attenuated *Salmonella typhimurium* vector). The DNA vaccine includes a polynucleotide that encodes a Fra-1 protein, such as a human or murine Fra-1 protein, together with a polynucleotide that encodes IL-18, such as human or murine IL-18. In a particularly preferred embodiment the polynucleotide construct encodes a polyubiquitinated Fra-1 protein, such as polyubiquitinated human Fra-1. Optionally, the vaccine also comprises a polynucleotide construct operably encoding IL-12.

The polynucleotide constructs can be a single DNA or RNA construct encoding the Fra-1, IL-18, and optionally IL-12. Alternatively the vaccine can comprise two or more polynucleotide constructs, for example, one construct encoding Fra-1, preferably polyubiquitinated Fra-1, another construct encoding IL-18, and optionally a third construct encoding IL-12. When more than one construct is utilized, preferably the constructs are operably incorporated into the same host vector.

The proteins and other gene products expressed by the DNA vaccines of the present invention have immunogenic and antigenic properties that stimulate an immune response against cancer cells, particularly breast cancer tumor cells in vaccinated patients, preferably human patients.

Preferred host vectors are attenuated bacterial vectors, such as attenuated *Salmonella typhimurium, Salmonella typhi, Shigella, Bacillus, Lactobacillus, BCG, Escherichia coli, Vibrio cholerae*, and *Campylobacter*. More preferably the host vector is an attenuated *Salmonella typhimurium* vector, most preferably a doubly attenuated aroA$^-$ dam$^-$ *S. typhimurium*.

In one method aspect of the present invention, a DNA vaccine is utilized to provide long term inhibition of tumor growth in a vaccinated patient. A DNA vaccine comprising a polynucleotide construct operably encoding a Fra-1 protein, preferably a polyubiquitinated Fra-1 protein and IL-18 in a pharmaceutically acceptable carrier is administered to a patient in need of inhibition of tumor growth. The vaccine is administered in an amount that is sufficient to elicit an immune response against tumor cells. Preferably the polynucleotide construct is operably incorporated in an attenuated bacterial vector such as an attenuated *S. typhimurium*. Preferably, the vaccine is administered orally to a patient suffering from a cancer, such as breast cancer, or a patient having an increased risk for developing such a cancer.

In another method aspect, a mammal is vaccinated against cancer cells to afford long term protection against developing the cancer. A DNA vaccine comprising a polynucleotide construct operably encoding a Fra-1 protein, preferably a polyubiquitinated Fra-1 protein and IL-18 in a pharmaceutically acceptable carrier, is administered to a mammal. The vaccine elicits a protective immune response in the mammal, which provides long term prevention of cancers for which Fra-1 is an antigen.

Yet another method aspect of the present invention is in vivo delivery of genetic material to a mammal. The method involves orally administering to a mammal doubly attenuated aroA⁻ dam⁻ *S. typhimurium* cells comprising a polynucleotide construct operably encoding a therapeutically useful gene product. The therapeutically useful gene product preferably is a tumor antigen capable of eliciting an immune response in the mammal against tumor cells or an immune stimulating molecule capable of stimulating the immune system of the mammal. In a preferred embodiment, the doubly attenuated aroA⁻ dam⁻ *S. typhimurium* cells comprise both a tumor antigen and an immune stimulating molecule.

The present invention also encompasses host cells transformed with a polynucleotide construct operably encoding a Fra-1 protein and IL-18, as well as plasmid vectors comprising a polynucleotide construct operably encoding a Fra-1 protein and IL-18.

The vaccines and transformed cells of the present invention are useful for treatment and prevention of various types of cancer. A patient suffering from breast cancer, or an increased risk of breast cancer, can particularly benefit from immunization by the vaccines of the present invention.

BRIEF DESCRIPTION OF THE DRAWINGS

In the Drawings, FIG. 1A schematically depicts the coding sequence of full-length, polyubiquitinated murine Fra-1 or IL-18, inserted into the pIRES plasmid (pUb-Fra-1 or pIL-18).

Figure 1A:
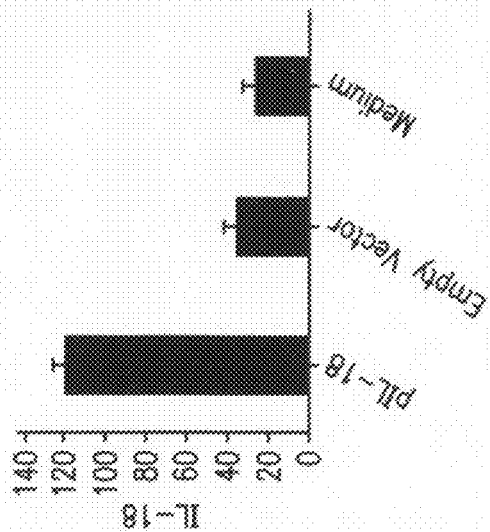
FIG. 1B depicts detection of protein expression by pUb-Fra-1 and pIL-18, demonstrated by Western blotting. Blots of cell lysates are shown from COS-7 cells transfected with either pUb-Fra-1 (lane 1) or pIL-18 (lane 2) as well as from a culture supernatant of pIL-18 transfected COS-7 cells (lane 3).
FIG. 1C demonstrates bioactivity of IL-18 (ng/ml), determined by ELISA in supernatants of KG-1 lymphoma cells that had been transfected with pIL-18.
FIG. 1D shows expression of EGFP activity in Peyer's Patches, determined in 6 week old Balb/c mice immunized by oral gavage with about $10^8$ cells per mouse of aroA⁻ dam⁻ bacteria transformed with pEGFP (S.T-GFP). Mice were sacrificed about 24 hours later and a fresh specimen of small intestine was taken after thoroughly washing with PBS. Fluorescence expression of EGFP was detected by confocal microscopy (right panel). H&E staining of mouse Peyer's Patches is also shown (left panel).

The line and arrows (a-e) indicate the inside borders of the Matrigel plug. Matrigel was implanted into mice, vaccinated with empty vector (a),pUb (b),pUb-Fra-1 (c), pIL-18 (d), pUb-Fra-1/pIL-18(e). The average fluorescence of Matrigel plugs from each group of mice is depicted by the bar graphs ($P<0.05$) (n=4; mean+SD).

FIG. 10 depicts the reported DNA nucleic acid sequence (SEQ IL NO: 1) and corresponding protein amino acid sequence (SEQ ID NO: 2) of human Fra-1.

FIG. 11 depicts the DNA nucleic acid sequence (SEQ IL NO: 3) and corresponding protein amino acid sequence (SEQ ID NO: 4) of murine Fra-1.

FIG. 12 depicts the reported DNA nucleic acid sequence (SEQ IL NO: 5) and corresponding protein amino acid sequence (SEQ ID NO: 6) of human IL-18.

FIG. 13 depicts the DNA nucleic acid sequence (SEQ IL NO: 7) and corresponding protein amino acid sequence (SEQ ID NO: 8) of murine IL-18.

FIG. 14 depicts the DNA nucleic acid sequence (SEQ IL NO: 9) and corresponding protein amino acid sequence (SEQ ID NO: 10) of ubiquitin.

DETAILED DESCRIPTION OF PREFERRED EMBODIMENTS

The term "polynucleotide construct" as used herein and in the appended claims means a synthetic DNA or RNA structure that can be transcribed in target cells to express a gene product. The construct can comprise a linear nucleic acid, such as a purified DNA, purified RNA, and the like, or DNA incorporated in a plasmid vector. Preferably, the polynucleotide is incorporated in a viral or bacterial vector, more preferably an attenuated viral or bacterial vector that is non-pathogenic, most preferably in an attenuated bacterial vector.

The term "gene product" and grammatical variations thereof, as used herein, includes proteins and polypeptides produced in a cell by gene expression processes.

As used herein, the term "immunity" refers to long term immunological protection against the virulent form of the infectious agent or tumor antigen. The term "immunization" refers to prophylactic exposure to an antigen of a pathogenic agent derived from a non-virulent source, which results in immunity to the pathogen in the treated subject.

The term "antibody", as used herein, refers to a molecule that is a glycosylated protein, an immunoglobulin, which specifically binds to an antigen.

The term "antigen", as used herein, denotes an entity bound by an antibody or receptor. The term "immunogen", as used herein denotes an entity that induces antibody production or binds to the receptor. Where an entity discussed herein is both immunogenic and antigenic, reference to it as either an immunogen or antigen is made according to its intended utility.

The term "conservative substitution", as used herein, denotes replacement of one amino acid residue by another, biologically similar residue. Examples of conservative substitutions include the substitution of one hydrophobic residue such as isoleucine, valine, leucine or methionine for another, or the substitution of one polar residue such as arginine for lysine and vice versa, glutamic acid for aspartic acid vice versa, or glutamine for asparagine and vice versa, and the like.

The term "substantially corresponds" in its various grammatical forms as used herein relating to peptide sequences means a peptide sequence as described plus or minus up to three amino acid residues at either or both of the amino- and carboxy-termini and containing only conservative substitutions along the polypeptide sequence.

The term "residue" in reference to amino acids, proteins and polypeptides is used herein interchangeably with the phrase amino acid residue. In reference to polynucleotides and nucleic acids the term "residue" is used interchangeably with the phrase nucleotide residue.

The term "polyubiquitinated" and grammatical variations thereof, in reference to a Fra-1 protein means that the Fra-1 is a fusion protein with four (4) ubiquitin molecules. A polynucleotide encoding ubiquitin and the corresponding amino acid sequence of ubiquitin are shown in FIG. 14.

Preferably, a polynucleotide construct utilized in the vaccines and transfected host cells of the present invention are also operably linked to regulatory elements needed for gene expression, which are well known in the art.

Preferably the polynucleotide construct, such as a DNA construct is operably incorporated in an expression vector, such as the pIRES expression vector available from Invitrogen, Inc., Carlsbad, Calif. Other suitable expression vectors are commercially available, for example, from BD Biosciences Clonetech, Palo Alto, Calif. Once incorporated in the expression vector, the DNA can be introduced into a host vector such as a live, attenuated bacterial vector by transfecting the host cell with the expression vector.

Useful polynucleotide constructs preferably include regulatory elements necessary for expression of polynucleotides. Such elements include, for example, a promoter, an initiation codon, a stop codon, and a polyadenylation signal. In addition, enhancers are often required for expression of a sequence that encodes an immunogenic target protein. As is known in the art, these elements are preferably operably linked to the sequence that encodes the desired protein. Regulatory elements are preferably selected that are compatible with the species to which they are to be administered.

Initiation codons and stop codons are preferably included as part of a nucleotide sequence that encodes the Fra-1 protein and IL-18 in a genetic vaccine of the present invention. The initiation and termination codons must, of course, be in frame with the coding sequences for the Fra-1 protein and IL-18.

Promoters and polyadenylation signals included in a vaccine of the present invention are preferably selected to be functional within the cells of the subject to be immunized.

Examples of promoters useful in the vaccines of the present invention, especially in the production of a genetic vaccine for humans, include but are not limited to promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, Cytomegalovirus (CMV) such as the CMV immediate early promoter, Epstein Barr Virus (EBV), Rous Sarcoma Virus (RSV) as well as promoters from human genes such as human actin, human myosin, human hemoglobin, human muscle creatine, and human metalothionein.

Examples of polyadenylation signals useful in the vaccines of the present invention, especially in the production of a genetic vaccine for humans, include but are not limited to SV40 polyadenylation signals and LTR polyadenylation signals.

In addition to the regulatory elements required for DNA expression, other elements can also be included in the DNA molecule. Such additional elements include enhancers. The enhancer can be, for example, human actin, human myosin, human hemoglobin, human muscle creatine and viral enhancers such as those from CMV, RSV and EBV.

Regulatory sequences and codons are generally species dependent. In order to maximize protein production, the regulatory sequences and codons are selected to be effective in the species to be immunized. One having ordinary skill in the art can readily produce DNA constructs that are functional in a given subject species.

The polynucleotide constructs utilized in the vaccines and transfected cells of the present invention can be "naked" DNA as defined in Restifo et al. *Gene Therapy* 2000; 7:89-92, the pertinent disclosure of which is incorporated by reference. Preferably, the polynucleotide is a DNA operably incorporated in a delivery vector. Useful delivery vectors include biodegradable microcapsules, immuno-stimulating complexes (ISCOMs) or liposomes, and genetically engineered attenuated live vectors such as viruses or bacteria.

Examples of suitable attenuated live bacterial vectors include *Salmonella typhimurium, Salmonella typhi, Shigella* species, *Bacillus* species, *Lactobacillus* species, *Bacille Calmette-Guerin (BCG), Escherichia coli, Vibrio cholerae, Campylobacter* species, or any other suitable bacterial vector, as is known in the art. Preferably the vector is an attenuated live *Salmonella typhimurium* vector. Most preferably, the vector is a doubly attenuated aroA⁻ dam⁻ *S. typhimurium*. Methods of transforming live bacterial vectors with an exogenous polynucleotide construct are well described in the art. See, for example, Joseph Sambrook and David W. Russell, *Molecular Cloning, A Laboratory Manual*, 3rd Ed., Cold Spring Harbor Laboratory Press, Cold Spring Harbor, N.Y. (2001) (Sambrook and Russell).

Preferred viral vectors include Bacteriophages, Herpes virus, Adenovirus, Polio virus, Vaccinia virus, and Avipox. Methods of transforming viral vector with an exogenous polynucleotide construct are also well described in the art. See, for example, Sambrook and Russell, above.

Liposome vectors are unilamellar or multilamellar vesicles, having a membrane portion formed of lipophilic material and an interior aqueous portion. The aqueous portion is used in the present invention to contain the polynucleotide material to be delivered to the target cell. It is generally preferred that the liposome forming materials have a cationic group, such as a quaternary ammonium group, and one or more lipophilic groups, such as saturated or unsaturated alkyl groups having about 6 to about 30 carbon atoms. One group of suitable materials is described in European Patent Publication No. 0187702, and further discussed in U.S. Pat. No. 6,228,844 to Wolff et al., the pertinent disclosures of which are incorporated by reference. Many other suitable liposome-forming cationic lipid compounds are described in the literature. See, e.g., L. Stamatatos, et al., *Biochemistry* 1988; 27:3917-3925; and H. Eibl, et al., *Biophysical Chemistry* 1979; 10:261-271. Alternatively, a microsphere such as a polylactide-coglycolide biodegradable microsphere can be utilized. A polynucleotide construct is encapsulated or otherwise complexed with the liposome or microsphere for delivery of the polynucleotide to a tissue, as is known in the art.

The method aspect of the present invention involves administering polynucleotides to the tissues of a mammal, such as a human, to elicit an immune response against cancer cells. In some preferred embodiments, the polynucleotides are administered orally, intramuscularly, intranasally, intraperitoneally, subcutaneously, intradermally, or topically. Preferably the vaccine is administered orally.

A DNA vaccine effective for eliciting an immune response against tumor cells comprises a polynucleotide construct that operably encodes a Fra-1 protein and the cytokine IL-18, an immune stimulating molecule that induces interferon-γ production by T cells and NK cells.

Without being bound by theory, it is believed that vaccination of a patient, such as a human patient, with a vaccine of the invention leads to selective expression of the Fra-1 protein and the IL-18 in cancerous cells. Increased presentation of the Fra-1 protein on the cancer cell surface, in combination with expression of immune stimulating IL-18, leads to an enhanced immune response against tumor cells that express Fra-1 proteins, such as breast cancer cells. Preferably the polynucleotide construct encodes a polyubiquitinated Fra-1 protein. Polyubiquitination of the Fra-1 protein is believed to target the Fra-1 protein to the proteosome, where the antigen can be degraded and processed, to be presented as a MHC class I antigen complex.

In a preferred method, a DNA vaccine can be utilized to provide long term inhibition of tumor growth in a patient treated with the vaccine. The DNA vaccine comprises a polynucleotide construct operably encoding a Fra-1 protein, such as a polyubiquitinated Fra-1 protein, IL-18, and a pharmaceutically acceptable carrier therefor. The vaccine is administered to a mammal in need of inhibition tumor growth in an amount that is sufficient to elicit an immune response against tumor cells.

Preferably, the mammal treated with a vaccine of the present invention is a human. A patient suffering from cancer, such as lung or colon carcinoma, breast tumors, or prostate tumors, and the like cancers, can benefit from immunization by the vaccines of the present invention. Most preferably the patient is a human patient suffering from breast cancer or an increased risk of breast cancer.

Vaccines of the present invention preferably are formulated with pharmaceutically acceptable carriers or excipients such as water, saline, dextrose, glycerol, and the like, as well as combinations thereof. The vaccines can also contain auxiliary substances such as wetting agents, emulsifying agents, buffers, adjuvants, and the like.

The vaccines of the present invention are preferably administered orally to a mammal, such as a human, as a solution or suspension in a pharmaceutically acceptable carrier, at a nucleic acid concentration in the range of about 1 to about 10 micrograms per milliliter. The appropriate dosage will depend upon the subject to be vaccinated, and in part upon the judgment of the medical practitioner administering or requesting administration of the vaccine.

The vaccines of the present invention can be packaged in suitably sterilized containers such as ampules, bottles, or vials, either in multi-dose or in unit dosage forms. The containers are preferably hermetically sealed after being filled with a vaccine preparation. Preferably, the vaccines are packaged in a container having a label affixed thereto, which label identifies the vaccine, and bears a notice in a form prescribed by a government agency such as the United States Food and Drug Administration reflecting approval of the vaccine under appropriate laws, dosage information, and the like. The label preferably contains information about the vaccine that is useful to an health care professional administering the vaccine to a patient. The package also preferably contains printed informational materials relating to the administration of the vaccine, instructions, indications, and any necessary required warnings.

The human FRA-1 nucleic acid sequence and its corresponding protein sequence have been reported by Wang et al. in the GENBANK® database of the National Center for Biotechnology Information, National Library of Medicine, Bethesda, Md., DNA Accession No. NM 005438, the disclosures of which are incorporated herein by reference. The murine FRA-1 polynucleotide sequence and its corresponding protein sequence have been reported by Strauseberg et al. in the GENBANK® database of the National Center for Biotechnology Information, National Library of Medicine, Bethesda, Md., DNA Accession No. BC052917, the disclosures of which are incorporated herein by reference.

The reported nucleic acid sequence encoding human Fra-1 (SEQ ID NO: 1), and its corresponding amino acid sequence (SEQ ID NO: 2) are provided in FIG. 10. The nucleic acid sequence encoding murine Fra-1(SEQ ID NO: 3), utilized in the Examples, and its corresponding amino acid sequence (SEQ ID NO: 4) are provided in FIG. 11.

The reported nucleic acid sequence encoding human IL-18 (SEQ ID NO: 5), and its corresponding amino acid sequence (SEQ ID NO: 6) are provided in FIG. 12. The nucleic acid sequence encoding murine IL-18 (SEQ ID NO: 7), utilized in the Examples, and its corresponding amino acid sequence (SEQ ID NO: 8) are provided in FIG. 13.

Preferably, the vaccines for the present invention comprise polynucleotide constructs that encode a Fra-1 protein, such as human Fra-1, murine Fra-1, and functional homologs thereof. The functional homologs preferably share at least about 70% amino acid sequence identity with the aforementioned proteins, more preferably at least about 80% amino acid sequence identity, most preferably at least about 90% amino acid sequence identity. Most preferably, the polynucleotide constructs encode a polyubiquitinated Fra-1 protein.

Ubiquitin is a highly conserved protein common to many mammalian species including humans, mice and rats. The nucleic acid sequence (SEQ ID NO: 9) encoding ubiquitin and its corresponding amino acid sequence (SEQ ID NO: 10) are shown in FIG. 14.

Preferably, the vaccines for the present invention comprise polynucleotide constructs that encode IL-18, such as human IL-18, murine IL-18, and functional homologs thereof. The functional homologs preferably share at least about 70% amino acid sequence identity with the aforementioned IL-18 proteins, more preferably at least about 80% amino acid sequence identity, most preferably at least about 90% amino acid sequence identity.

Interleukin-12 (also know as NK cell stimulatory factor) is a 70,000 dalton molecular weight heterodimeric cytokine protein comprising p40 and p35 chains that activates NK cells and induces CD4 T cell differentiation to Th1-like cells. IL-12 plays an important role in a variety of immune responses. Optionally, the vaccines of the present invention can comprise a polynucleotide construct that operably encodes IL-12, which is an immune stimulating molecule.

Due to the inherent degeneracy of the genetic code, a polynucleotide that encodes substantially the same or a functionally equivalent amino acid sequences to native (i.e., naturally occurring) Fra-1 protein, IL-18, or IL-12 can be used in the vaccines of the invention. Such polynucleotides include those which are capable of hybridizing to the native Fra-1, IL-18, or IL-12 DNA sequence, as well as allelic variants thereof, and the like. Preferably the polynuceotide of the functionally equivalent homologs share at least about 70% nucleic acid sequence identity with the DNA encoding the aforementioned native Fra-1, IL-18 or IL-12 proteins, more preferably at least about 80% nucleic acid sequence identity, most preferably at least about 90% nucleic acid sequence identity.

Altered nucleic acid sequences that can be used in accordance with the invention include deletions, additions or substitutions of different nucleotide residues resulting in a sequence that encodes the same or a functionally equivalent gene product. The gene product itself may contain deletions, additions or substitutions of amino acid residues within the Fra-1 protein, IL-18 or IL-12, which result in a silent change, thus producing a functionally equivalent molecule. Such amino acid substitutions (e.g., conservative substitutions) may be made on the basis of similarity in polarity, charge, solubility, hydrophobicity, hydrophilicity, and/or the amphipathic nature of the residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine.

As used herein, a functionally equivalent Fra-1 protein refers to a polypeptide having substantially the same transcription inducing activity as its counterpart naturally occurring Fra-1 protein. A functionally equivalent immune stimulating gene product, such as IL-18 or IL-12 refers to a polypeptide having substantially the same immunomodulating activity as its counterpart naturally occurring immune stimulating gene product.

The nucleic acid sequences encoding the Fra-1 protein and the immune stimulating gene products (e.g., IL-18 and IL-12) useful in the vaccines of the invention may be engineered to alter the coding sequences for a variety of purposes including, but not limited to, alterations that modify processing and expression of the gene product. For example, mutations may be introduced using techniques that are well known in the art, e.g. site-directed mutagenesis, to insert new restriction sites, to alter glycosylation patterns, phosphorylation, and the like.

Another aspect of the present invention is a method of vaccinating a mammal against cancer. The method comprises administering to the mammal a vaccine of the present invention, as described herein, in an amount sufficient to elicit an immune response against cancer cells. Preferably the mammal is a human.

In another aspect, the present invention also encompasses transformed host cells, which have been transfected with a vector comprising a polynucleotide construct operably encoding a Fra-1 protein, IL-18, and optionally, IL-12, as described herein. The host cell can be a prokaryotic cell or a eukaryotic cell. Preferably the host cell is transformed with a polynucleotide construct encoding a polyubiquitinated Fra-1 protein.

The present invention also provides isolated plasmid vectors comprising a polynucleotide construct operably encoding a Fra-1 protein (e.g., a polyubiquitinated Fra-1), IL-18, and optionally, IL-12. The vectors are useful for transfecting host cells, such as attenuated bacterial cells, for preparing the vaccines of the invention.

The following examples are provided to further illustrate the features and embodiments of the present invention, and are not meant to be limiting.

Animals, Bacterial Strains and Cell Lines.

Female Balb/c mice, 6-8 weeks of age, were purchased from The Scripps Research Institute Rodent Breeding Facility. The attenuated *S. typhimurium* strain RE88 (aroA⁻ dam⁻) was kindly provided by Remedyne Corporation, (Santa Barbara, Calif.). Bacterial strain Top 10 was purchased from Invitrogen, (Carlsbad, Calif.) and bacteria were grown routinely at about 37° C. in LB broth or on agar plates (EM SCIENCE, Darmstadt, Germany), supplemented, when required, with about 50 μg/ml ampicillin. The murine D2F2 breast cancer cell line was obtained from ATCC (American Type Culture Collection, USA) and cultured in Dulbecco's Modified Eagle's Medium (DMEM) supplemented with about 10% (vol/vol) fetal bovine serum (FBS). All animal experiments were performed according to the National Institutes of Health Guide for the Care and Use of Laboratory Animals.

EXAMPLE 1

Construction of Expression Vectors

Two constructs were made based on the pIRES vector (Invitrogen). The first, pUb-Fra-1, encoded polyubiquitinated, full-length murine Fos-related antigen-1 (Fra-1). The second, pIL-18, encoded murine Interleukin-18 (IL-18). The empty vectors with or without a polyubiquitin sequence, served as controls. Protein expression of Fra-1 and IL-18 was demonstrated by Western blotting. IL-18 protein expression was found in both cell lysates and culture supernatants. The bioactivity of murine IL-18 in the cell supernatants was measured by an ELISA assay (RD systems, Minneapolis Minn.) using the production of IFN-γ in KG-1 lymphoma cells as an indicator, as described by Kawashima, et al., 2001, *Arthritis Rheum.*, 44: 550-560. The pUb-Fra-1 construct included the murine Fra-1 DNA sequence shown in FIG. 11 (SEQ ID NO: 3) and four repeats of the ubiquitin DNA sequence shown in FIG. 14 (SEQ ID NO: 9). The pIL-18 construct included the murine IL-18 DNA sequence shown in FIG. 13 (SEQ ID NO: 7).

EXAMPLE 2

Transduction and Expression of *S. typhimurium* with DNA Vaccine Plasmids

Attenuated *Salmonella typhimurium* (aroA$^-$ dam$^-$) were transduced with DNA vaccine plasmids by electroporation. Briefly, a single colony of bacteria was inoculated into about 3 ml of Luria-Bertani (LB) medium, and then harvested during mid-log phase growth and washed twice with ice-cold water. Freshly prepared bacteria (about $1\times10^8$) were then mixed with plasmid DNA (about 2 μg) on ice in a 0.2 cm cuvette and electroporated at about 2.5 KV, 25 μF, and 200 Ω. The bacteria were transformed with the following plasmids: empty vector, pUb, pUb-Fra-1, pIL-18 or both pUb-Fra-1 and pIL-18 together, indicated as pUb-Fra-1/pIL-18. After electroporation, the bacteria were immediately removed from the cuvette and placed into a sterile culture tube containing about 1 ml of LB broth medium and incubated with moderate shaking for about 30 minutes at about 37° C. The bacteria were centrifuged and then plated onto LB plates with about 50 μg/ml ampicillin. Resistant colonies harboring the DNA vaccine gene(s) were cultured and stored at about −70° C. after confirmation of the coding sequence.

EXAMPLE 3

Detection of EGFP Expression

Figure 1B:
Figure 1B:
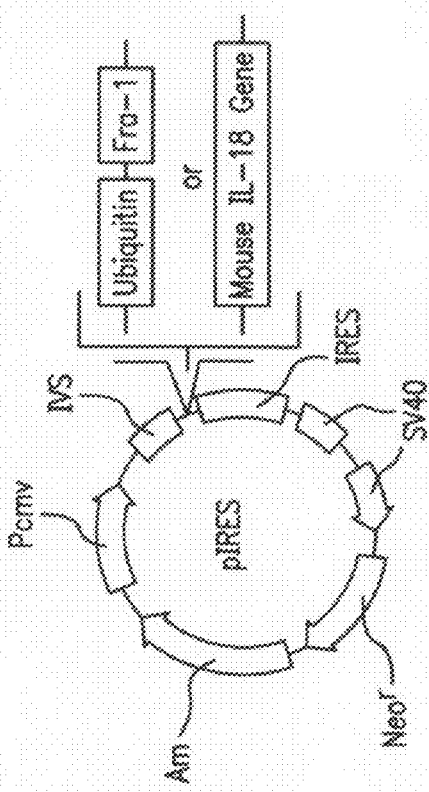
Figure 1D:
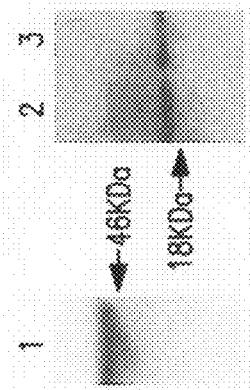

Enhanced green fluorescent protein (EGFP) expression by aroA$^-$ dam$^-$ *S. typhimurium* was used to obtain direct evidence for DNA transfer from the bacterial carrier to Peyer's Patches and to establish that protein expression took place efficiently and successfully. EGFP expression was tested using the doubly attenuated strain *S. typhimurium* harboring the gene (S.T-GFP). Mice were administered about $1\times10^8$ bacteria by oral gavage, and about 24 hours thereafter, these animals were sacrificed and biopsies collected from the small intestine washed thoroughly with phosphate buffered saline (PBS). The fresh specimens were checked for EGFP expression in Peyer's Patches by confocal microscopy or saved for further hematoxylin and eosin (H&E) staining. The results are shown in FIG. 1D.

EXAMPLE 4

Protein Detection by Western Blotting

To detect protein production, COS-7 cells were transfected with the pUb-Fra-1 or pIL-18 plasmid using a calcium phosphate transfection kit based on the manufacturer's instructions (Invitrogen). After about 24 hours, the cells were harvested and lysed and protein concentrations were determined with a BCA kit (Pierce, Rockford, Ill.). Protein (about 30 μg) of each sample was purified by electrophoresis on 16% Tris-Glycine gels and then transferred onto nitrocellulose membranes (Invitrogen) that were subjected to about 150 mA for about 30 minutes. Membranes were blocked for about 2 hours by about 5% nonfat dry milk in PBS containing about 0.2% Tween 20. Western blot analysis was performed with anti-Fra-1 Ab (Santa Cruz Biotechnology, Santa Cruz, Calif.) or anti-mouse IL-18 mAb (MBL, Nagoya, Japan). Films were developed using a chemiluminescence protocol provided by the manufacturer (Pierce, Rockford, Ill.). The results are shown in FIG. 1B.

EXAMPLE 5

Oral Immunization and Tumor Cell Challenge

Figure 2:
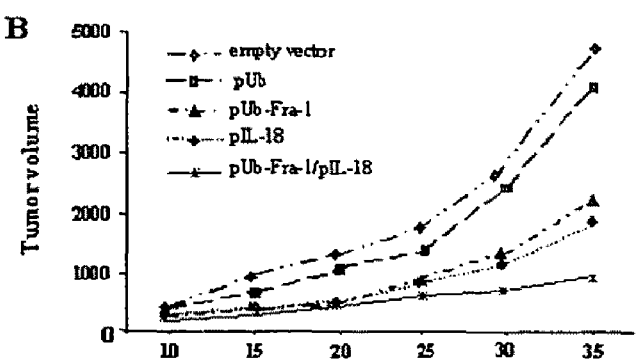
FIG. 2A shows suppression of pulmonary metastases of D2F2 breast carcinoma. Lung metastases were induced by intravenous injection of about $5 \times 10^5$ D2F2 cells about 1 week after the last vaccination. The experiment was terminated about 28 days after tumor cell inoculation and the extent of tumor foci on the lung surface determined. Results are expressed as metastatic score, i.e., the % lung surface covered by fused tumor foci. 0=0%; 1=<20%; 2=20-50%; and 3=>50%.
FIG. 2B depicts tumor growth, analyzed in mice challenged subcutaneously with about $1 \times 10^6$ D2F2 tumor cells about 1 week after the last vaccination in each of respective treatment or control groups. Tumor growth was determined by microcaliper measurements and tumor volume was calculated according to the equation: $0.5 \times \text{width}^2 \times \text{length}$.
FIG. 2C illustrates survival curves representing results for 8 mice in each of the respective treatment and control groups. Surviving mice were tumor free unless otherwise stated.
Figure 2:
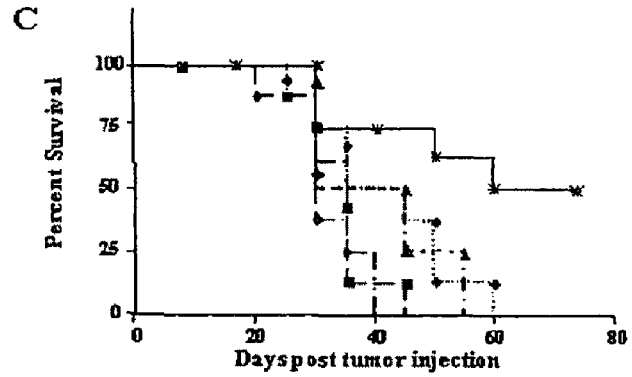

Balb/c mice were divided into five experimental groups (n=8) and immunized three times at two week intervals by oral gavage with about 100 μl PBS containing about $1\times10^8$ doubly mutated *S. typhimurium* harboring either empty vector, pUb, pUb-Fra-1, pIL-18 or pUb-Fra-1/pIL-18 as prepared in Example 2. All mice were challenged subcutaneously into the right flank with a lethal dose of about $1\times10^6$ D2F2 breast cancer cells or by intravenous injection with about $0.5\times10^6$ of D2F2 cells about 1 week after the last immunization to induce primary tumor or experimental pulmonary metastases, respectively. In the subcutaneous tumor model, mice were examined twice each week until the tumor became palpable, after which its diameter was measured in two dimensions with a microcaliper every other day. In the pulmonary metastases model, mice were sacrificed about 4 weeks after intravenous injection. Metastasis scores were determined as percentage of lung surface covered by fused metastases as follows: a score of 0=0%, a score of 1=less than about 20%, a score of 2=about 20 to about 50%, a score of 3=greater than about 50%. The results are shown in FIG. 2A and FIG. 2B.

EXAMPLE 6

Cytotoxicity Assay

Figure 3:
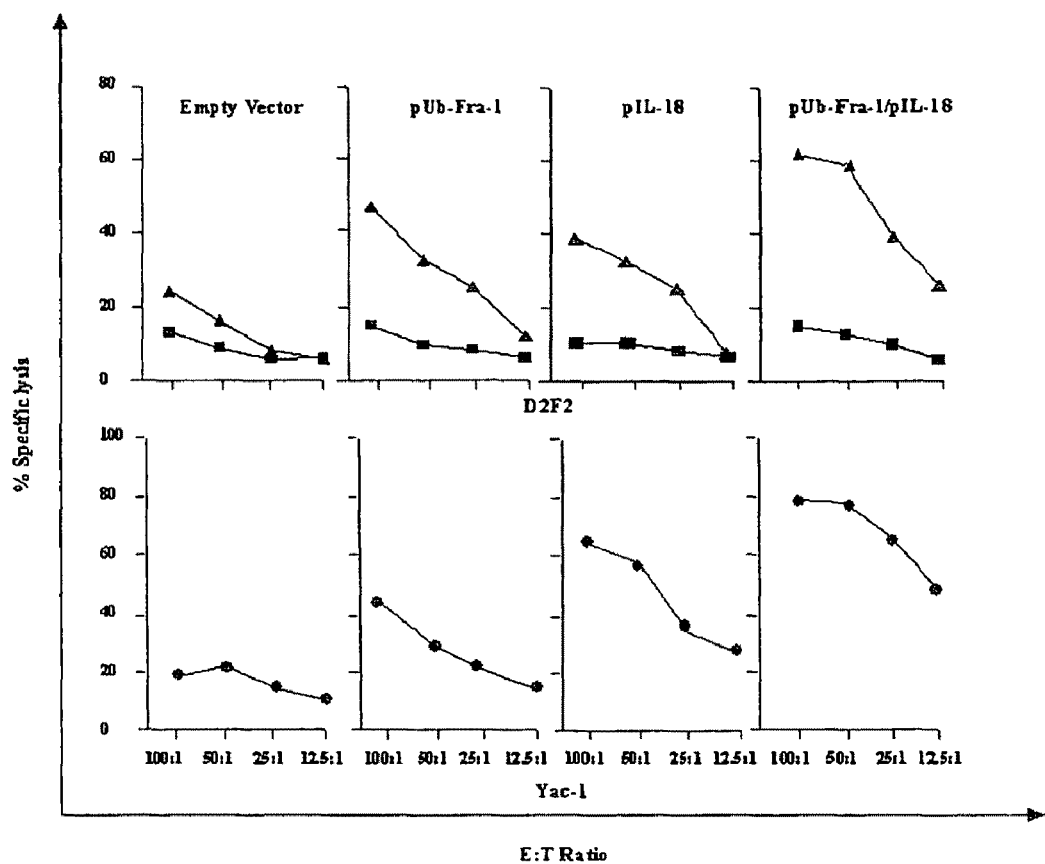
FIG. 3 depicts cytotoxic activity of splenocytes isolated from Balb/c mice after vaccination with experimental or control DNA vaccines about 2 weeks after challenge with D2F2 tumor cells and analyzed for their cytotoxic activity in a $^{51}$Cr-release assay at different E:T cell ratios. The top panel depicts specific lysis mediated by CD8⁺T cells against D2F2 target cells (▲), which was blocked by an anti MHC-class I Ab (H-2K$^d$/H-2D$^d$) (■). The bottom panel depicts lysis mediated by NK cells (●) against Yac-1 target cells. Each value shown represents the mean of 8 animals.

Cytotoxicity was measured by a standard $^{51}$Cr-release assay. Splenocytes were harvested from Balb/c mice about 2 weeks after challenge with about $0.5\times10^6$ D2F2 breast carcinoma cells and subsequently cultured for about 3 days at about 37° C. in complete T-STIM culture medium (Beckton Dickinson, Bedford, Mass.). Both D2F2 and Yac-1 cells were used as targets. These cells were each labeled with about 0.5 mCi of $^{51}$Cr, and incubated at about 37° C. for about 4 hours with effector cells at various effector to target cell ratios. The percentage of specific target cell lysis was calculated with the formula $[(E-S)/(T-S)]\times100\%$, where E is the average experimental release, S is the average spontaneous release, and T is the average total release. The results are shown in FIG. 3.

EXAMPLE 7

Flow Cytometric Analysis

Figure 4:
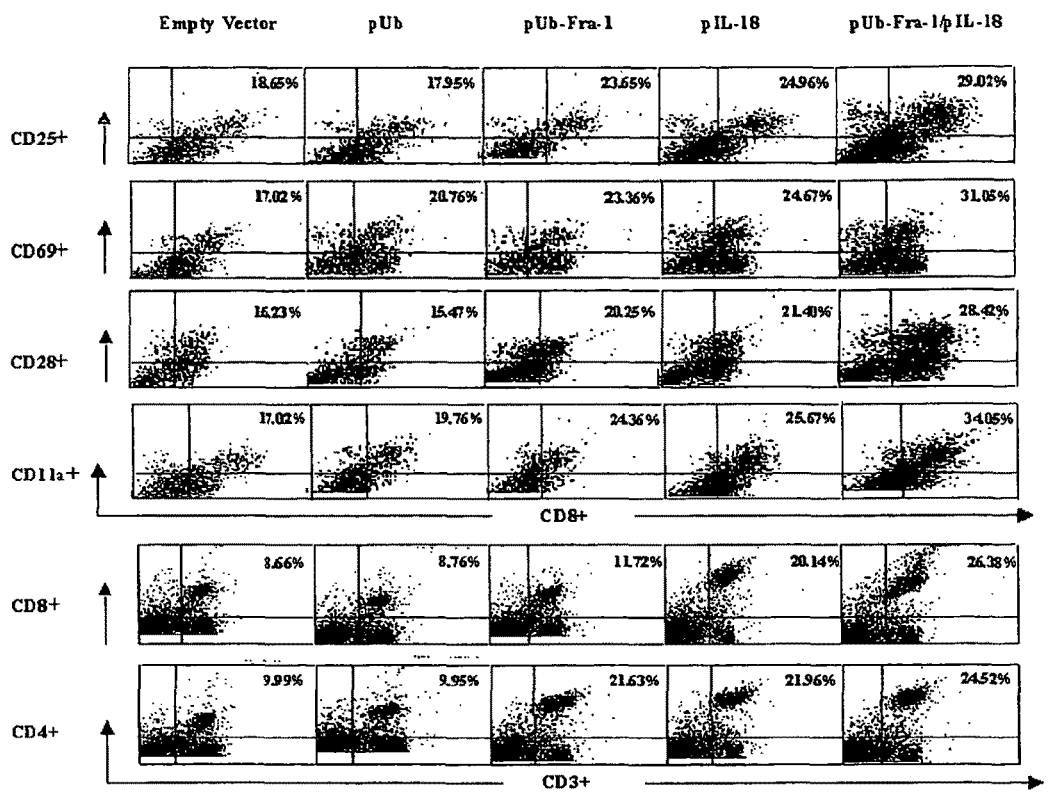
FIG. 4 shows a FACS analysis of splenocytes from Balb/c mice immunized with the DNA vaccine, then challenged with tumor cells. Two-color flow cytometric analyses were performed with single-cell suspensions of splenocytes. Anti-CD25, CD69, CD28 and CD11a Ab were used in PE conjugated form in combination with FITC-conjugated anti-mouse mAb directed against CD8⁺T cells. PE-labeled anti-CD8 and anti-CD4 Ab were used in combination with FITC-conjugated anti-mouse mAb CD3. Each value represents the mean for 4 mice.
Figure 5:
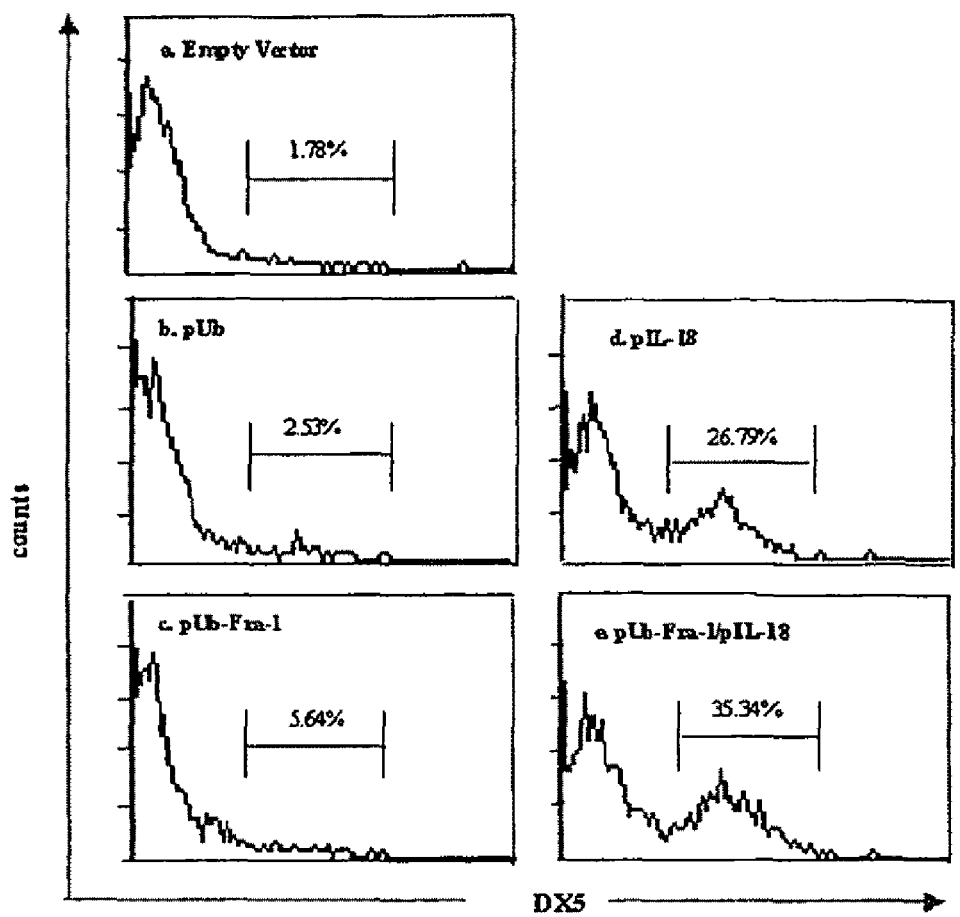
FIG. 5 shows FACS analysis of splenocytes with anti-DX5 mAb, demonstrating the activation of NK cells after DNA vaccination. The experimental setting is similar to that of FIG. 4. Percentages refer to the percentage of cells in an assay gated for DX5 expression. A representative histogram plot is shown for each group with the value depicting the mean for 4 mice.
Figure 6:
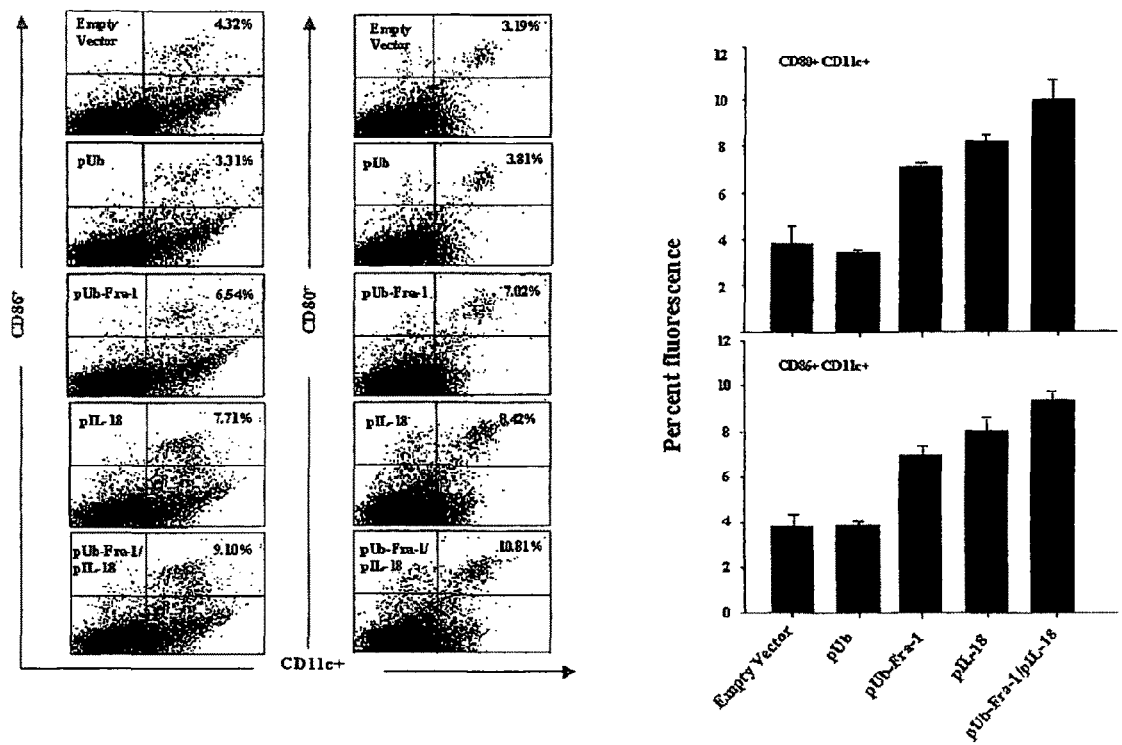
FIG. 6 shows that the pUb-Fra-1/pIL-18 vaccine of the invention enhanced the expression of costimulatory molecules. In a similar evaluation to that depicted in FIG. 4, two-color flow cytometric analyses were performed with single-cell suspensions prepared from mouse splenocytes obtained about 30 days after tumor cell challenge. Splenocytes were stained with FITC-labeled anti-CD11c Ab in combination with PE-conjugated anti-CD80 or CD86 Ab. Shown is the percent fluorescence of cell surface expressions of these two costimulatory molecules in a representative mouse. The data from each group (n=4) is displayed in the bar graph (mean+SD).

Activation markers of T cells and NK cells as well as CD80 (B 7.1) and CD86 (B 7.2) costimulatory molecules were measured by two-color flow cytometric analysis with a BD Biosciences FACScan. T cell activation was determined by staining freshly isolated splenocytes from successfully vaccinated mice with anti-CD8-FITC or anti-CD3-FITC Ab in combination with PE-conjugated anti-CD25, CD11a, CD28 or CD69 Ab. Activation of NK cell markers was measured with FITC-labeled anti-NK-1.1 Ab in combination with PE-conjugated anti-DX5 Ab. Costimulatory molecules on APCs were detected by PE-conjugated anti-CD80 or CD 86 Ab in combination with FITC-labeled CD11c Ab. All reagents were obtained from BD Pharmingen (La Jolla, Calif.). The results are shown in FIGS. 4, 5, and 6.

EXAMPLE 8

Cytokine Release Assay

Figure 7:
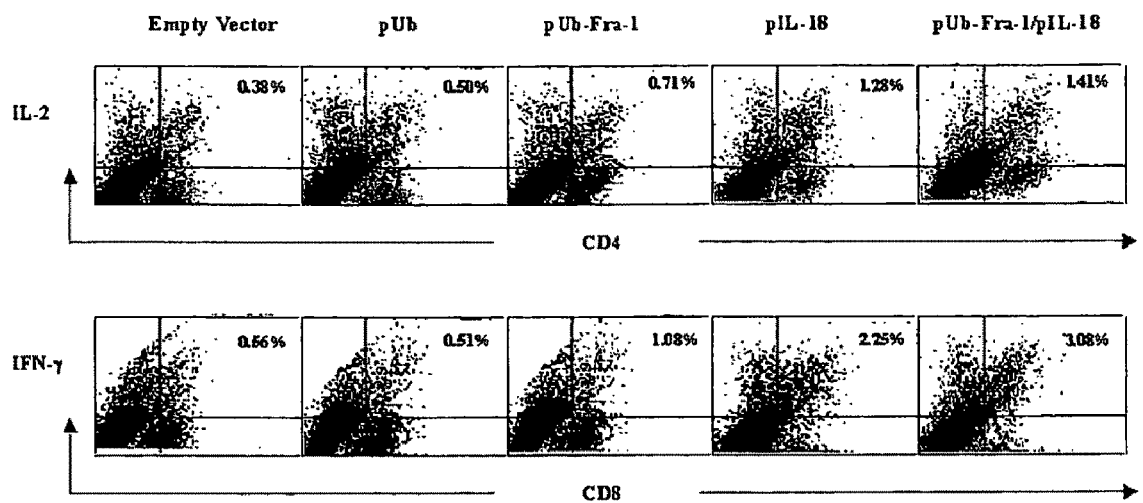
FIG. 7 demonstrates cytokine expression from splenocytes obtained about 2 weeks after tumor cell challenge and stained with FITC-anti CD4 or CD8 Ab. Cells were fixed, permeabilized and subsequently stained with PE labeled anti-IFN-γ or anti IL-2 Ab to detect the intracellular expression of these cytokines. A representative dot plot is shown for each group with the value depicting the mean for 8 mice.
Figure 8:
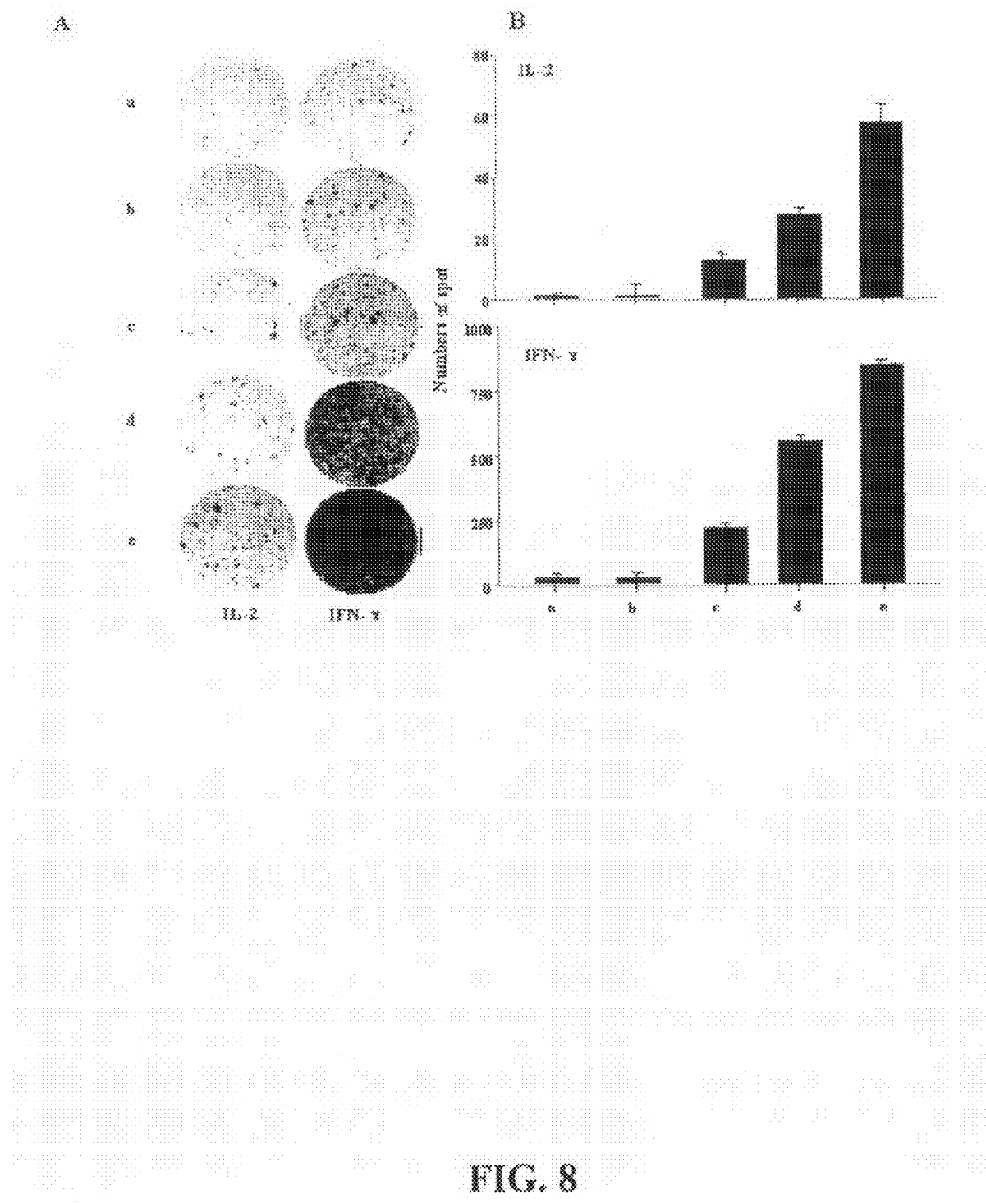
FIG. 8A shows a representative ELISPOT assay as spot formation per well induced by empty vector (a), pUb(b), pUb-Fra-1(c), pIL-18(d) and pUb-Fra-1/pIL-18(e).
FIG. 8B shows the mean spot distribution of each well in each experimental and control group for the ELISPOT assay shown in FIG. 8A (n=4, mean+SD).

Flow cytometry was utilized for detection of intracellular cytokines and the ELISPOT assay to measure single cell cytokine release. To this end, splenocytes were collected about 2 weeks after D2F2 tumor cell challenge from all experimental groups of mice, and culture for about 24 hours in complete T cell medium with irradiated D2F2 cells as described. Preincubated cells were suspended with about 1 µg purified 2.4G2 Ab (BD Pharmingen) to block nonspecific staining. The cells were washed and then stained with about 0.5 µg FITC conjugated anti-CD3$^+$ Ab. After washing two times, cells were fixed and stained with about 1 µg/ml PE conjugated with anti-IL2 or anti-IFN-γ Ab for flow cytometric analysis. All Ab were obtained from BD Pharmingen. Immunospot plates (BD Bioscience, San Diego, Calif.) were coated overnight at about 4° C. with capture Ab specific for either IFN-γ or IL-2. The plates were then blocked with FBS (about 10% in RPMI 1640 culture medium). D2F2 cells (about $1\times10^4$/ml) were irradiated with about 1000 Gy, plated and stimulated with mitogen. Splenocytes were collected about 2 weeks after intravenous D2F2 tumor cell challenge from all experimental groups of mice, and were plated in complete RPMI 1640 medium (about $1\times10^6$/ml, Hyclone). After overnight incubation, the cells were washed, first with deionized water, and then with washing buffer. Thereafter, Avidin-HRP (about 1:100) was added following incubation with biotinylated anti-mouse IFN-γ Ab (about 2 µg/ml) and IL-2 (about 2 µg/ml). The spots were developed with AEC development solution, and plates read by IMMUNOSPOT® Sc Analysis (BD Bioscience). Digitalized images were analyzed for areas in which color density exceeded background by an amount based on a comparison of experimental wells. The results are shown in FIGS. 7, 8A and 8B.

EXAMPLE 9

Evaluation of Anti-Angiogenic Effects

Figure 9:
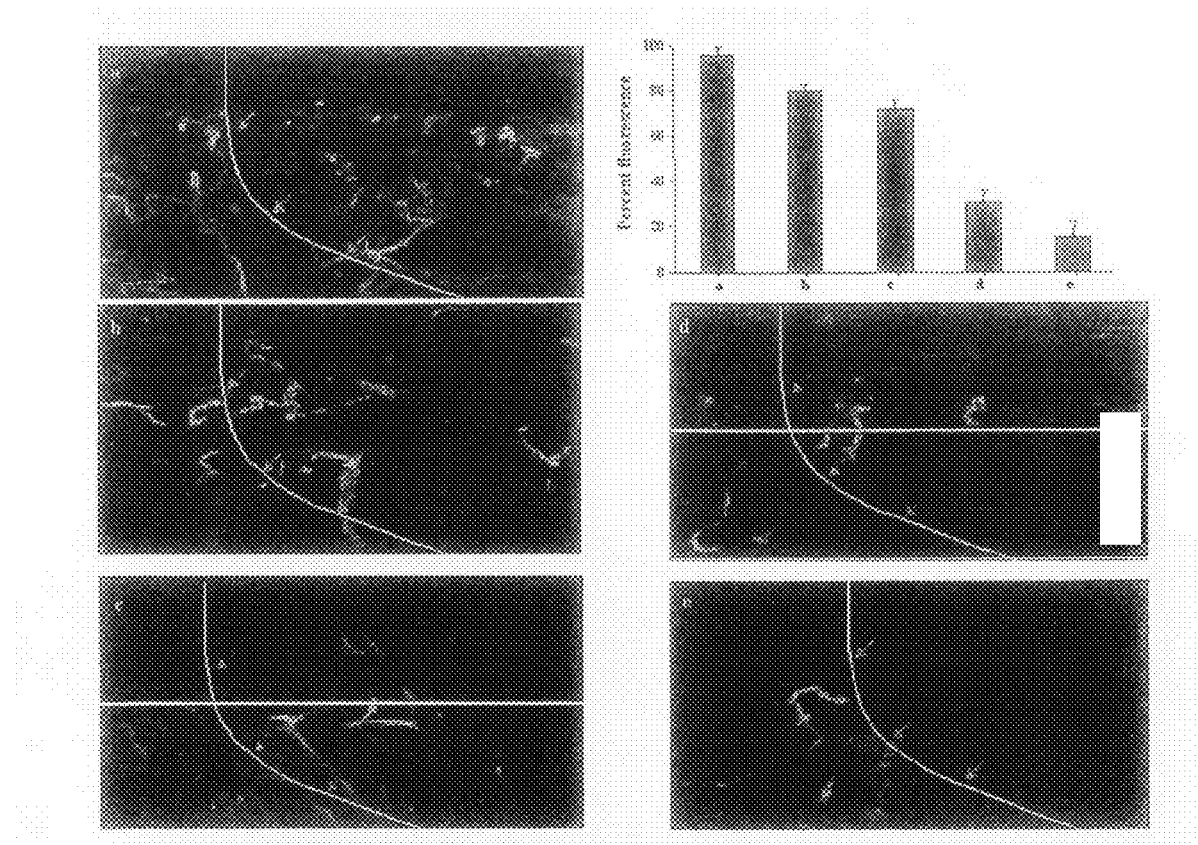
FIG. 9 depicts photomicrographs of Matrigel implants from Balb/c mice (n=8) vaccinated 3 times at about 2 week intervals with doubly attenuated *Samonella typhimurium* vaccines. About two weeks after the last vaccination, Matrigel (about 0.5 ml) containing murine FGF-2 (about 400 μg) and D2F2 cells (about $1 \times 10^5$) were subcutaneously implanted into the sternal region of mice and plugs removed for evaluation about 6 days later. Quantification of vessel growth and staining of endothelium was determined by fluorimetry or confocal microscopy, respectively, using FITC-labeled Isoletin B4. Matrigel implants were harvested from mice and photographed with the use of confocal microscope.

Balb/c mice were vaccinated as described above in Example 5. Two weeks after the last vaccination, mice were subcutaneously injected in the sternal region with about 500 µl growth factor-reduced Matrigel (BD Biosciences) containing about 400 ng/ml murine FGF-2 (PeproTech, Rocky Hill, N.J.) and D2F2 tumor cells (about $1\times10^4$/ml) which were irradiated with about 1000 Gy. In all mice, except for 2 control animals, endothelium tissue was stained about 6 days later by intravenous injection into the lateral tail vein with about 200 µl of about 0.1 mg/ml fluorescent *Bandeiraea simplicifolia* lectin I, Isolectin B4 (Vector Laboratories, Burlingame, Calif.). About thirty minutes later, mice were sacrificed and Matrigel plugs excised and evaluated macroscopically. Lectin-FITC was then extracted from about 100 µg of each plug in about 500 µl of RIPA lysis buffer (PBS about 1% NP-40, about 0.5% sodium deoxycholate, about 0.1% SDS) with the help of a tissue grinder. Solid materials were pelleted by centrifugation and lectin-FITC content in the buffer quantified by fluorimetry at about 490 nm. Background fluorescence found in the two non-injected control mice was subtracted in each case. The results are shown in FIG. 9.

Discussion.

Eukaryotic expression vectors based on the pIRES vector backbone, namely pUb-Fra-1 and pIL-18 (FIG. 1A) were prepared. Protein expression of pUb-Fra-1 and pIL-18 was demonstrated by transient transfection of each vector into COS-7 cells, and by performing Western blots on the respective cell lysates (pUb-Fra-1 or pIL-18) and supernatants (pIL-18) with anti-Fra-1 and anti-IL-18 Ab. The results indicated that all constructs produced protein of the expected molecular mass with IL-18 being expressed in its active form at 18 kD (FIG. 1B, lane 2) and Fra-1 as a 46 KDa protein (FIG. 1B, lane 1). Protein expression of IL-18 was also detected in the culture supernatant of transfected cells (FIG. 1B, lane 3). Importantly, the biofunctional activity of IL-18 was demonstrated by ELISA in supernatants of cells transfected with pIL-18. (FIG. 1C).

DNA encoding pUb-Fra-1 and pIL-18 was successfully released from the attenuated bacterial vaccines of the present invention and entered Peyer's Patches in the small intestine (FIG. 1D) to be subsequently transcribed by APCs, processed in the proteasome and presented as MHC-peptide complexed to T cells. To this end, mice were administered by oral gavage about $1\times10^8$ dam$^-$, aroA$^-$ attenuated *S. typhimurium* harboring a polyubiquitinated Fra-1 polynucleotide and an IL-18 polynucleotide, as well as various control vaccines. After about 24 hours these animals were sacrificed and biopsies were collected from the thoroughly washed small intestine. In fact, the doubly attenuated bacteria harboring EGFP (S.T-GFP) exhibited strong EGFP fluorescence (FIG. 1D), suggesting not only that such bacteria can transfer a target gene to Peyer's Patches, but also that plasmids encoding each individual gene can successfully express their respective proteins. Importantly, because of the aroA$^-$ dam$^-$ mutation, these doubly attenuated bacteria do not survive very long since neither EGFP activity nor live bacteria could be detected in immunized animals after about 72 hours. However, EGFP expression was detected in adherent cells, most likely APCs such as DCs and macrophages from Peyer's Patches following oral administration of *Salmonella typhimurium* harboring the eukaryotic EGFP expression plasmid. Taken together, these findings suggest that both plasmid transfer to and protein expression in eukaryotic cells did take place.

An administered DNA vaccine encoding murine Ub-Fra-1 and secretory IL-18, carried by attenuated *S. typhimurium*, induces protective immunity against subcutaneous tumor growth and pulmonary metastasis of D2F2 breast carcinoma. A marked inhibition was observed for both subcutaneous tumor growth and disseminated pulmonary metastases in Balb/c mice challenged about 1 week after the third vaccination with the pUb-Fra-1/pIL-18 vaccine of the invention by either intravenous (FIG. 2A) or subcutaneous (FIG. 2B) injection of D2F2 murine breast cancer cells. In contrast, animals vaccinated with only the empty vector (pIRES) or the vector encoding only ubiquitin (pUb), carried by attenuated bacteria, all uniformly revealed rapid subcutaneous tumor growth and extensive dissemination of pulmonary metastases. Importantly, the life span of about 60% of successfully vaccinated Balb/c mice (5/8) was tripled in the absence of any detectable tumor growth up to about 11 weeks after tumor cell challenge (FIG. 2C).

Immunization with a DNA vaccine of the invention induces tumor-specific immunity capable of killing breast cancer cells in vitro either by MHC class I Ag-restricted $CD8^+$T cells or by NK cells. To this end, $CD8^+$T cells were isolated from splenocytes of groups of Balb/c mice vaccinated as described above. The data depicted in FIG. 3 indicate that only $CD8^+$T cells isolated from splenocytes of mice immunized with the vaccine of the invention encoding pUb-Fra-1/pIL-18 were effective in killing D2F2 breast cancer cells in vitro at different effector-to-target cell ratios. In contrast, controls such as $CD8^+$T cells isolated from mice immunized with only the empty vector vaccines carried by attenuated S. typhimurium produced solely background levels of tumor cell lysis (FIG. 3). The $CD8^+$T cell-mediated killing of D2F2 cells was specific as demonstrated by the fact that syngeneic prostate cancer target cells (RM-2) lacking Fra-1 were not lysed. Importantly, the $CD8^+$T cell-mediated tumor cell lysis was MHC class I antigen-restricted as evidenced by addition of about 10 μg/ml of anti-$H-2K^d/H-2D^d$ Ab, which specifically inhibited lysis of D2F2 cells (FIG. 3).

NK cells were involved in tumor cell killing, as demonstrated by a standard 4 hour $^{51}$Cr-release assay using NK-specific Yac-1 cells as targets for splenocytes from Balb/c mice immunized and challenged with D2F2 breast cancer cells. Only immunization with the vaccine of the invention containing pUb-Fra-1/pIL-18 or a vaccine containing pIL-18 alone led to significant lysis of Yac-1 target cells by NK cells. In contrast, control immunizations were ineffective (FIG. 3).

The interaction between IL-18 and active Th1 cells and NK cells is important for achieving both optimal antigen specific T cell and NK cell responses.

The vaccines harboring either pUb-Fra-1/pIL-18 or pIL-18 alone upregulated the expression of T and NK cell activation markers, respectively. This was evident from an increase in expression of CD25, the high affinity IL-2R α-chain, CD69, an early T cell activation antigen, and CD11a, which is important for the initial interaction between cells and DCs as well as regular T cell markers $CD4^+$ and $CD8^+$ (FIG. 4). Additionally, it has been reported that NK cells play a partial role in the process of anti-tumor immune response. For that reason, spleen cells obtained from mice successfully immunized with DNA vaccines along with the control groups were assayed with anti-DX5. As shown in FIG. 5, this regimen dramatically increased the DX5 expression on NK cells, which is especially important for NK cytotoxicity.

Furthermore, T cell activation is dependent on up-regulated expression of costimulatory molecules CD80 (B 7.1) and CD86 (B 7.2) on DCs to achieve optimal ligation with CD28 expressed on T cells. In this regard, FACS analyses of splenocytes obtained from syngeneic BALB/c mice, successfully immunized with a DNA vaccine of the invention clearly demonstrated upregulation of CD80 and CD86 expression by about 2- to 3-fold over controls (FIG. 6).

The release of pro-inflammatory cytokines IL-2 and IFN-γ from T cells is a well-known indication of T cell activation in secondary lymphoid tissues. Consequently, IL-2 and IFN-γ release was measured both intracellularly with flow cytometry (FIG. 7), and at the single cell level with ELISPOT (FIG. 8) in vaccinated mice. Vaccination with the pUb-Fra-1/pIL-18 containing vaccine of the invention and subsequent challenge with tumor cells resulted in a dramatic increase of IFN-γ and IL-2 release over that of splenocytes from animals vaccinated with control vaccines by both analysis methods.

Distinct suppression of angiogenesis was induced by the pUb-Fra-1/pIL-18 DNA vaccine of the invention in a Matrigel assay. This was evident from the marked decrease in vascularization following vaccination, as evaluated by relative fluorescence after in vivo staining of endothelium with FITC-conjugated lectin. Differences were visible macroscopically, as shown in FIG. 9 depicting representative examples of Matrigel plugs removed from vaccinated mice about 6 days after their injection. FITC-lectin staining clearly revealed suppression of angiogenesis indicated by a significantly decreased vascularization of Matrigel plugs after vaccination with the pUb-Fra-1/pIL-18-containing vaccine of the invention and to a somewhat lesser extent with a pIL-18-containing vaccine alone, but not with vaccines encoding only pUb-Fra-1, pUb or the empty vector control (FIG. 9).

The design of effective cancer vaccines remains a major challenge for tumor immunotherapy. The vaccines of the present invention meet this challenge by providing a novel DNA vaccine encoding a transcription factor, Fra-1, which is overexpressed in breast cancer and reported to be significantly associated with invasion and growth of this neoplasm in combination with an immune system stimulating molecule IL-18. The present results demonstrate that peripheral T cell tolerance against the Fra-1 transcription factor can be broken by an oral DNA vaccine encoding full length murine Fra-1, fused with mutant polyubiquitin, and further modified by co-transformation with a gene encoding secretory murine IL-18.

The immunological mechanisms and effector cells involved in the tumor protective immunity induced by the vaccines of the present invention clearly indicate a prominent cellular immune response by both T and NK cells. Activation of immune effector cells is highly correlated with upregulation of IFN-γ. In fact, the regulation of IFN-γ expression is one of the most tightly controlled processes of the cellular immune response. Production of IFN-γ, was induced by the DNA vaccines of the present invention, and was found to be substantially limited to activated $CD4^+$ and $CD8^+$ T cells, as well as NK cells. For each of these cell types, IFN-γ secretion is further moderated by the availability of IFN-γ inducing cytokines such as IL-2, IL-12 and TNF-α, which arise from accessory cells following activation. IL-18 reportedly is a potent antiangiogenic cytokine, both in vitro and in vivo. Consequently, the vaccines of the invention were designed to express a combination of Fra-1 and secretory IL-18. Activation of both T- and NK cells was significantly augmented after immunization with the multi-functional DNA vaccine of the invention, as indicated by marked upregulation of a series of T- and NK cell activation markers. The present data demonstrate that immunization with a pUb-Fra-1/pIL-18 DNA vaccine induces and enhances the expression of the costimulatory molecules CD80 and CD86 on $CD11c^+$ and MHC class II antigen positive APCs, suggesting that the capability of these APCs for processing and presentation of tumor-specific antigen was significantly enhanced by the vaccine.

The marked elevation in production of proinflammatory cytokines IFN-γ and IL-2 detected by intracellular cytokine staining and single cell cytokine release also demonstrated T cell activation after immunization with vaccines of the present invention. Upregulation of CD25 was also observed together with increased production of IL-2 by activated T-cells. Tumor angiogenesis was found to be effectively suppressed only in groups of mice that were immunized with the pUb-Fra-1/pIL-18 vaccine of the invention and to a lesser extent with pIL-18 alone in the D2F2 breast cancer model as indicated by suppression of vessel formation and regression of growing blood vessels.

Successful stimulation of effective CD8+T cell-mediated MHC class 1 antigen-restricted tumor protective immunity with the oral DNA vaccine of the invention was most likely aided by ubiquitination leading to more effective antigen presentation. A DNA vaccine encoding murine Fra-1 lacking in ubiquitin was less effective in inducing tumor protective immunity than the vaccine expressing ubiquitinated Fra-1.

An important aspect of DNA vaccine design is the selection of an optimally effective carrier to deliver the target gene to the immune system. In a particularly preferred embodiment, the vaccine as targeted to secondary lymphoid organs, such as Peyer's Patches, in the small intestine. This approach is designed to achieve a non-invasive administration of the vaccine, as well as long-term protection by single or multiple vaccinations. In addition, oral vaccines can have the advantage of ease of preparation, storage, and transport. In this regard, live, attenuated bacterial carriers that harbor polynucleotides encoding an antigen, combined with a powerful adjuvants, are attractive vehicles or oral delivery of vaccines. Current DNA vaccine delivery vehicles include replicating attenuated strains of intracellular bacteria like *Salmonella typhimurium, Listeria monocytogenes* and *Mycobacterium bovis* as well as *Bacillus Calmette Gurein (BCG)*. These DNA vaccine delivery vehicles have been reported to induce a broad spectrum of both mucosal and systemic immune responses. Moreover, the use of this natural route of entry could prove to be of benefit since many bacteria, like *Salmonella*, egress from the gut lumen via M cells into Peyer's Patches and migrate even eventually into lymph nodes and spleen, thus allowing natural targeting of DNA vaccines to inductive sites of the immune system.

A particularly effective attenuated bacterial vector for oral delivery is a novel, doubly mutated strain of *S. typhimurium* (dam−, aroA−). This strain of bacteria provides a number of advantages over other attenuated bacterial strains. For example, DNA adenine methylase (dam−) mutants of *S. typhimurium* have been reported to be highly attenuated and useful as live vaccines in a murine model of infection. Additionally, dam− mutants do not cause a transient state of nonspecific immune suppression, indicating their potential usefulness as a vaccine carrier to deliver heterologous antigens to immune inductive sites. Although dam− mutants reportedly are unable to cause disease in mice, transient bacteria have reportedly remained after several weeks in terminal organs. Thus, in order to completely abolish the systemic presence of the bacteria, a second mutation (aroA−) was introduced, which inhibits the synthesis of aromatic amino acids and causes the bacteria to die after just a few passages. The dam− aroA− double mutant, which was undetectable in systemic tissues, indicating a safer and less toxic *Salmonella*, was consequently chosen as a preferred vaccine carrier.

By using doubly mutated bacteria as a vaccine carrier, Fra-1 antigen targets appropriate pathways of major histocompatibility (MHC) class I antigen processing and presentation. In addition, an adequate cytokine milieu is generated upon vaccination, which effectively promotes antigen-specific responses. The most prominent advantage of this vaccine carrier vehicle is its capability to directly target DNA vaccines to Peyer's Patches, which harbor immature dendritic cells (DCs), B cells, T cells and macrophages. These immune system cells are important immune effector cells necessary for an immune response induced by a DNA vaccine. Among these cells, DCs are important antigen presenting cells that efficiently mediate antigen processing, transport and presentation to lymphoid tissues for the initiation of T cell responses.

Taken together, the present results demonstrate that the transcription factor, Fra-1, is a suitable target for induction of a T cell-mediated specific immune response against breast cancer cells and that the design of a DNA vaccine, lead to effective antigen processing and presentation. The co-expression of secretory IL-18 by the vaccines of the present invention acts as a powerful and natural adjuvant for further activation of both CD8+ and CD4+ T cells as well as NK cells, leading to the production of IFN-γ and IL-2 as well as the suppression of angiogenesis in tumor tissues.

Numerous variations and modifications of the embodiments described above can be effected without departing from the spirit and scope of the novel features of the invention. It is to be understood that no limitations with respect to the specific embodiments illustrated herein are intended or should be inferred. It is, of course, intended to cover by the appended claims all such modifications as fall within the scope of the claims.

We claim:

1. A DNA vaccine suitable for eliciting an immune response against cancer cells that overexpress Fra-1, the vaccine comprising a polynucleotide construct operably encoding a Fra-1 protein and IL-18 in a pharmaceutically acceptable carrier.

2. The DNA vaccine of claim 1 wherein the polynucleotide construct is operably incorporated in a vector.

3. The DNA vaccine of claim 2 wherein the vector is an attenuated bacterial vector.

4. The DNA vaccine of claim 3 wherein the attenuated bacterial vector is selected from the group consisting of attenuated *Salmonella typhimurium, Salmonella typhi, Shigella, Bacillus, Lactobacillus*, BCG, *Escherichia coli, Vibrio cholerae*, and *Campylobacter*.

5. The DNA vaccine of claim 1 wherein the polynucleotide construct encodes a Fra-1 protein having an amino acid sequence selected from the group consisting of SEQ ID NO: 2 and SEQ ID NO: 4.

6. The DNA vaccine of claim 1 wherein the polynucleotide construct encodes IL-18 having an amino acid sequence selected from the group consisting of SEQ ID NO: 6 and SEQ ID NO: 8.

7. The DNA vaccine of claim 1 wherein the polynucleotide construct comprises a polynucleotide encoding a human or murine Fra-1 protein, and having a nucleic acid sequence selected from the group consisting of SEQ ID NO: 1 and SEQ ID NO: 3.

8. The DNA vaccine of claim 1 wherein the polynucleotide construct comprises a polynucleotide encoding a human or murine IL-18, and having a nucleic acid sequence selected from the group consisting of SEQ ID NO: 5 and SEQ ID NO: 7.

9. The DNA vaccine of claim 1 wherein the polynucleotide construct further encodes IL-12.

10. The DNA vaccine of claim 1 wherein the polynucleotide construct comprises an Fra-1 polynucleotide having a nucleic acid sequence selected from the group consisting of SEQ ID NO: 1, and SEQ ID NO: 3 and an IL-18 polynucleotide having a nucleic acid sequence selected from the group consisting of SEQ ID NO: 5, and SEQ ID NO: 7.

11. A method of inhibiting tumor growth in a mammal having a Fra-1 overexpressing tumor and comprising the step of administering to the mammal an effective immunological response eliciting amount of a DNA vaccine comprising a polynucleotide construct operably encoding a Fra-1 protein and IL-18 in a pharmaceutically acceptable carrier, whereby the mammal exhibits an immune response elicited by vaccine and specific to tumor cells.

12. The method of claim 11 wherein the polynucleotide construct encodes IL-18 having an amino acid sequence selected from the group consisting of SEQ ID NO: 6 and SEQ ID NO: 8.

13. The method of claim 11 wherein the polynucleotide construct comprises a polynucleotide encoding a human or murine IL-18, and having a nucleic acid sequence selected from the group consisting of SEQ ID NO: 5 and SEQ ID NO: 7.

14. The method of claim 11 wherein the mammal is a human.

15. The method of claim 11 wherein the polynucleotide construct is operably incorporated in an attenuated bacterial vector.

16. The method of claim 15 wherein the attenuated bacterial vector is selected from attenuated *Salmonella typhimurium, Salmonella typhi, Shigella, Bacillus, Lactobacillus*, BCG, *Escherichia coli, Vibrio cholerae*, and *Campylobacter*.

17. The method of claim 15 wherein the vaccine is administered orally.

18. An isolated transformed host cell transfected with a polynucleotide construct operably encoding a Fra-1 protein and IL-18.

19. A method of vaccinating a mammal against a Fra-1 overexpressing cancer, the method comprising the step of administering to the mammal an effective immunological response eliciting amount of a DNA vaccine comprising a polynucleotide construct operably encoding a Fra-1 protein and IL-18 in a pharmaceutically acceptable carrier.

20. The method of claim 19 wherein the vaccine is administered orally.

21. A method of delivery of genetic material to a mammalian cell in vivo comprising orally administering to a mammal a polynucleotide construct operably encoding a therapeutically useful gene product comprising a Fra-1 protein and IL-18.

* * * * *